US007087248B2

(12) United States Patent
Minamitake et al.

(10) Patent No.: US 7,087,248 B2
(45) Date of Patent: Aug. 8, 2006

(54) PHARMACEUTICAL COMPONENT BASED ON HUMAN PARATHYROID HORMONE AND A PHARMACEUTICAL COMPOSITION FOR INTRANASAL ADMINISTRATION COMPRISING THE COMPONENT

(75) Inventors: Yoshiharu Minamitake, Gunma (JP); Tetsu Ono, Tatebayashi (JP); Koji Kawanishi, Tatebayashi (JP); Yuji Suzuki, Ashikaga (JP)

(73) Assignee: Daiichi Asubio Pharma Co., Ltd., Tokyo (JP)

( * ) Notice: Subject to any disclaimer, the term of this patent is extended or adjusted under 35 U.S.C. 154(b) by 353 days.

(21) Appl. No.: 10/312,726

(22) PCT Filed: Jun. 29, 2001

(86) PCT No.: PCT/JP01/05674

§ 371 (c)(1),
(2), (4) Date: Dec. 30, 2002

(87) PCT Pub. No.: WO02/02136

PCT Pub. Date: Jan. 10, 2002

(65) Prior Publication Data

US 2005/0107292 A1    May 19, 2005

(30) Foreign Application Priority Data

Jun. 30, 2000  (JP)  ............................. 2000-237717
Jun. 30, 2000  (JP)  ............................. 2000-237718

(51) Int. Cl.
*A61K 35/55*  (2006.01)
*A61K 38/00*  (2006.01)
*C07K 14/00*  (2006.01)

(52) U.S. Cl. .................... 424/562; 514/12; 514/21; 530/324

(58) Field of Classification Search ............. 424/562; 514/2, 12; 530/324
See application file for complete search history.

(56) References Cited

U.S. PATENT DOCUMENTS 4,086,196 A * 4/1978 Tregear ..................... 530/324
5,856,138 A * 1/1999 Fukuda ..................... 435/69.4
5,977,070 A * 11/1999 Piazza et al. ............... 514/12

FOREIGN PATENT DOCUMENTS

| EP | 515228 | 11/1992 |
|----|--------|---------|
| EP | 672682 | 9/1995 |
| JP | 64-16799 | 1/1989 |
| WO | 97/14429 | 4/1997 |

OTHER PUBLICATIONS

W. M. Law, Jr., et al. "Preparation of Synthetic Bovine Parathyroid Hormone Fragment 1-34 for Pareneral use in Human Studies;" *Journal of Clinical Endocrinology and Metabolism*, vol. 56, No. 6, pp. 1335-1337 (1983).

Muawia M. Ibrahim, et al. "Maintenance of Normocalcemia by Continuous Infusion of the Synthetic Bovine Parathyroid Hormone (1-34) in Parathyroidectomized Rats;" *Calcified Tissue International*, vol. 34, No. 6, pp. 553-557 (1982).

* cited by examiner

*Primary Examiner*—Karen Cochrane Carlson
*Assistant Examiner*—Marsha Tsay
(74) *Attorney, Agent, or Firm*—Armstrong, Kratz, Quintos, Hanson & Brooks, LLP

(57) ABSTRACT

A medical component comprising a human parathyroid hormone peptide or its derivative, and acetic acid contained at a concentration less than its chemical equivalent with respect to the human parathyroid hormone peptide or to its derivative. Since in the medical component acetic acid, which is present as a salt of or attached to the peptide or its derivative, has been reduced to an amount less than chemical equivalent with respect to the human parathyroid hormone peptide or its derivative, a medical component, which is highly stable and will ensure an excellent use feeling when introduced into a pharmaceutical composition, is obtained.

12 Claims, 6 Drawing Sheets

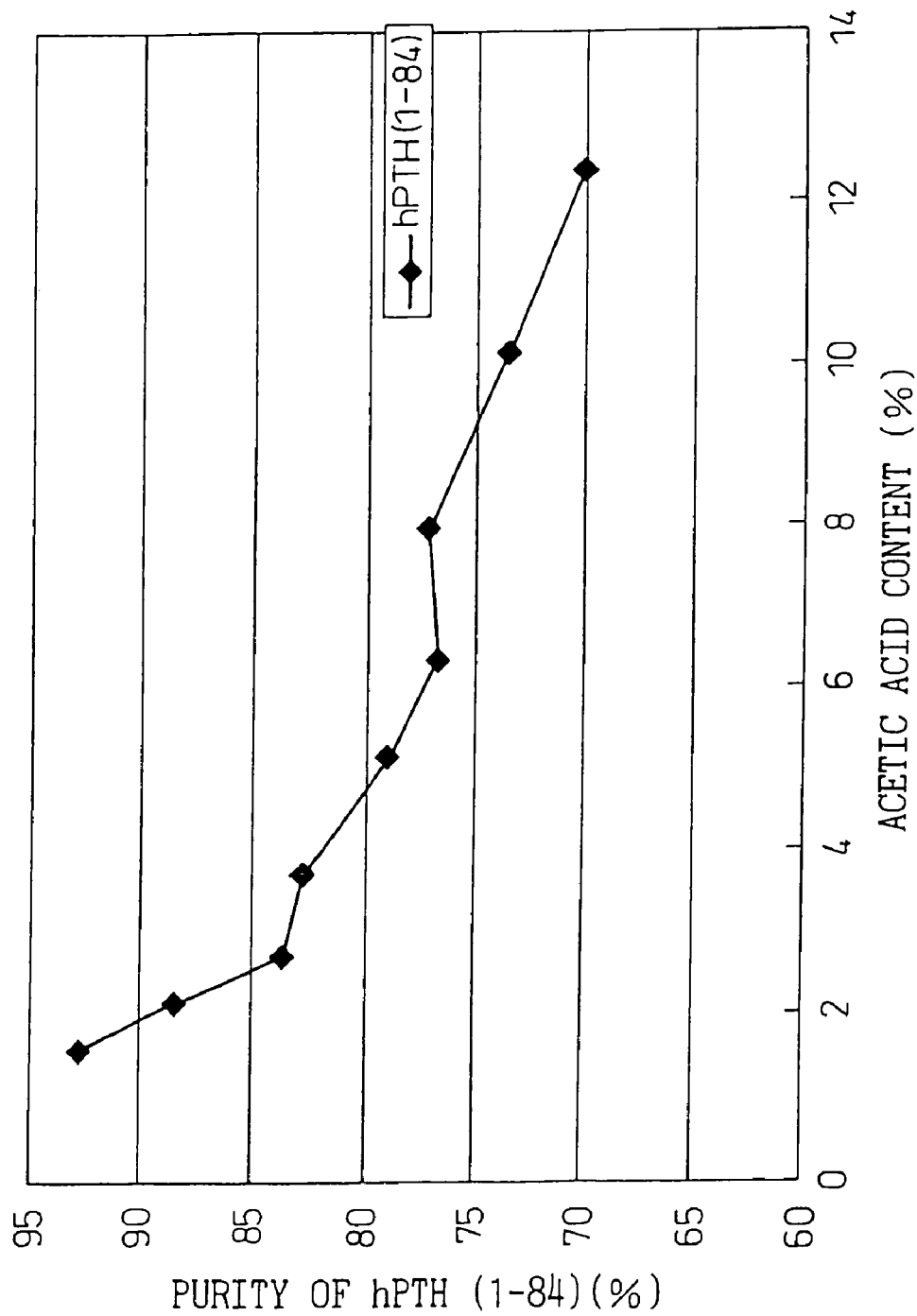

PHARMACEUTICAL COMPONENT BASED ON HUMAN PARATHYROID HORMONE AND A PHARMACEUTICAL COMPOSITION FOR INTRANASAL ADMINISTRATION COMPRISING THE COMPONENT

FIELD OF THE INVENTION

The present invention relates to a pharmaceutical component based on human parathyroid hormone which has an excellent stability, and ensures a good use feeling when used as a component of a pharmaceutical composition. In a further aspect, this invention relates to a pharmaceutical composition based on human parathyroid hormone for intranasal administration which is suitable for a long term use.

BACKGROUND ART

The peptides of human parathyroid hormone (to be referred to as "hPTH" hereinafter) are biologically active peptides which are responsible for bone metabolism, and have an strong activity to develop bones (Aurbach et al., Recent Progr. Horm. Res., 1972, vol. 28, p. 35). The hPTH is a peptide typically composed of 84 amino acid residues (hPTH(1-84)). A derivative, hPTH(1-34), from hPTH(1-84) composed of 34 amino acid residues designated as amino acid Nos. 1-34 of hPTH(1-84) has been also known to have the same pharmacological activity as does hPTH(1-84) (Tregear et al., Hoppe-Seyler's Z. Physiol. Chem., 1974, vol. 355, p. 415). The amino acid sequences of hPTH(1-84) and hPTH(1-34) are given as Sequence Nos. 1 and 2 in the Sequence Listing, respectively.

Calcitonin and bisphosphonate or therapeutic agents used for the treatment of osteoporosis exhibit their therapeutic effects by inhibiting bone resorption, whereas hPTH(1-84) and hPTH(1-34) stimulate bone formation, or bone metabolism involved in the bone formation. Thus, those peptides have been expected to serve as a new therapeutic agent of osteoporosis (Lane et al., J. Clin. Invest., 1998, vol. 102, pp. 1627–1633).

It has been reported, when hPTH(1-34) is subcutaneously applied to humans at a certain dose once weekly, it will increase the bone mineral content, while, when the same agent is similarly applied at a dose one fifth the previous one but once daily for five days successively, it will also increase the bone of mineral density (BMD) significantly (Sone et al., Miner Electrolyte Metab., 1995, vol. 21, pp. 232–235). In animal experiments it has been shown that hPTH, when given subcutaneously at a certain dose once weekly, will cause less BMP to bones than is observed when it is given divisional (Tawaragi et al., Osteoporosis International, vol. 6, suppl. 1, 1996, p. 245). This suggests a maximum therapeutic effect from hPTH will be obtained when hPTH is given daily at a small dose over a long period than when it is given at a large dose for a short period with a long interval between successive doses. If a small dose of hPTH given continuously over a long period will ensure an therapeutic effect equal to or more excellent than does a large dose given intermittently for a short period, this prescription will be also desirable from the view-point of small doses of hPTH being probably free from the adverse effects on the digestive and cardiovascular organs which are known for high dose administrations of hPTH.

Also, injections would be unsuitable to be used for the treatment of the patient with osteoporosis who will usually require a long term treatment, because the patient should then receive the treatment under the management of a physician; feel a more or less pain during treatment; and visit the physician's office regularly for treatment which would be a burden to the patient.

In view of this, there is a need for a nasal drug which would allow the patient to easily take it at home daily over a long period with no undue pain and burden imposed upon the patient.

However, for a nasal drug to be safely used continuously over a long period it is absolutely necessary that the drug should be smoothly absorbed through the nasal mucosa; have no irritating action against the nasal mucosa; and give an excellent use feeling, because the nasal mucosa is very sensitive to the irritating action of a medicine or an additive thereof. Particularly, for such a drug as the one prepared from hPTH which is expected to give a therapeutic effect when used over a long period, an excellent use feeling is very important when it is intended to be used for intranasal administration. In order to prepare a nasal drug which is acceptable even when used continuously over a long period, it is important to select the active agent in the form of a medicament or of its salt, and proper additives, to determine their effective concentrations, and to optimize their combination. The factors responsible for the use feeling of a nasal drug involve the odor and irritating activity of the drug. Thus, the kinds of medicaments or additives used for a nasal drug and their concentrations are very limited.

There is a commercially available product prepared from hPTH, that is, an injection containing a 5-acetate of hPTH (1-34) which is used as a diagnostic agent for assaying the functional activity of parathyroid (whose generic name is teriparatide acetate and which is provided by Asahi Kasei Kogyo Corp.). However, no intranasal drug based on hPTH is available that will give a satisfactory use feeling in terms of odor and irritability.

Japanese Patent Laid-Open No. 64-16799 describes that, when hPTH(1-34) is purified, it is mixed with acetic acid which is used for the purification process, and the acetic acid content in individual products vary widely from lot to lot, making it difficult to obtain products containing a uniform amount of acetic acid, and that introduction of acetic acid to the product will lead to a reduced activity of the product.

The same document further discloses a method suitable for improving the stability of hPTH(1-34) wherein a lyophilized composition of hPTH(1-34) based on the use of tartaric acid is utilized. However, tartaric acid is so highly acidic that an agent containing it will not be suitable for intranasal administration.

Japanese Patent Laid-Open No. 2-111 discloses a powdery composition for intranasal administration based on a water soluble organic acid which has been developed to improve the nasal absorption of hPTH(1-34) a biologically active peptide such as hPTH (1-34). However, the composition would not be suitable for a long term use, because it will directly irritate the nasal mucosa, depending on the kind and amount of coexistent organic acid.

As discussed above, no intranasal drug based on hPTH that is acceptable even when used over a long period, and ensures an excellent use feeling as well as good stability and absorption has been developed.

DISCLOSURE OF INVENTION

This invention aims at providing a pharmaceutical component based on hPTH which is highly stable, when used as a component of a pharmaceutical composition, and gives an excellent use feeling. In a still other aspect, this invention aims at providing a pharmaceutical composition for intranasal administration based on hPTH which will allow a long term use.

To meet the object of providing a pharmaceutical composition for intranasal administration as described above, the present inventors had studied hard, and reached a finding that an hPTH preparation conventionally prepared is unsatisfactory because it will give an acidic odor and irritation when administered to the nasal mucosa, and that this inconvenience is ascribed to acetic acid which is used in the purification process and exists in very small amount as the constituent of a salt of hPTH or an adherent. Based on this finding, they prepared a pharmaceutical component whose acetic acid content is reduced as compared with the previous one, assessed it and surprisingly found that the component in question is highly stable, gives an excellent use feeling when incorporated in a pharamceutical composition for, and presents with a property of being safely combined with the appropriate amounts of functional components which will be added for the improvement of absorption and stability, as well as with a carrier and excipient which are usually used during preparing medicines. Thus, they achieved this invention.

To put it more specifically, the present invention relates to a pharmaceutical component comprising hPTH and acetic acid whose content is kept less than a certain chemical equivalent with respect to the weight of hPTH. In a still other aspect, this invention relates to a pharamceutical composition for intranasal administration which contains hPTH as its active ingredient, and which also contains acetic acid whose content is kept less than a certain chemical equivalent with respect to the weight of hPTH.

BRIEF DESCRIPTION OF THE DRAWINGS

FIG. 7 shows the purity levels of hPTH(1-84) of the hPTH(1-84) preparations containing various acetic acid content after the preparations have been stored at 80° C. for 15 hours.

DESCRIPTION OF THE EMBODIMENTS

Figure 1:
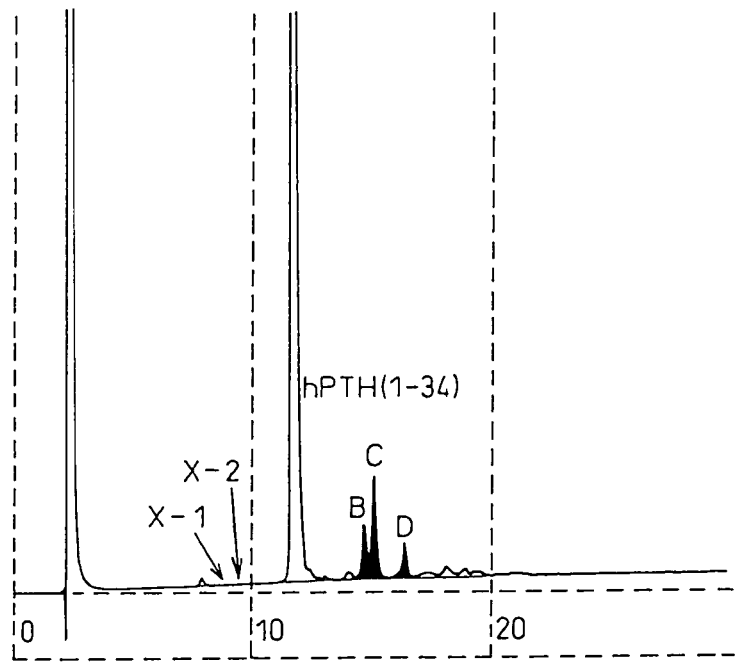
FIG. 1 shows a reverse phase HPLC chromatogram obtained from an hPTH(1-34) preparation as acetic acid content being 9.5% after it has been stored at 40° C. for six months.

According to this invention, hPTH includes peptides which are involved in bone metabolism, have a strong stimulating effect on the formation of bones, and have an activity to increase the concentration of calcium in serum, that is, a natural type hPTH(1-84) comprising 84 amino acid residues, and its derivatives.

For example, the hPTH may include hPTH(1-84) (Biochemistry 17, 5723(1978); Kimura et al., Biochem. Biophys. Res. Commun., vol. 114, p. 493, 1983), hPTH(1-38) (Japanese Patent Laid-Open No. 57-81448), hPTH(1-34) (Japanese Patent Laid-Open No. 9-29600; Takai et al., Peptide Chemistry, p. 187, 1979), hPTH(1-34)$NH_2$ (Japanese Patent Laid-Open No. 58-96052), [$Nle^{8,18}$]hPTH(1-34) and [$Nle^{8,18}$, $Tyr^{34}$]hPTH(1-34) (Japanese Patent Laid-Open No. 55-113753), [$Nle^{8,18}$]hPTH(1-34)$NH_2$ (Japanese Patent Laid-Open No. 61-24598), [$Nle^{8,18}$, $Tyr^{34}$]hPTH(1-34)$NH_2$ (Japanese Patent Laid-Open No. 60-34996), hPTH(1-37) (Japanese Patent Presentation [Kohyo] No. 5-505594), hPTH(2-84), hPTH(3-84), hPTH(4-84), hPTH(5-84), hPTH(6-84), hPTH(7-84), and hPTH(8-84) (Japanese Patent Presentation [Kohyo] No. 4-505259), etc. These hPTHs can be obtained by the methods based on genetic engineering techniques or chemical synthesis techniques as described in the above documents, or by the methods equivalent with the former.

Generally speaking, when a physiologically active peptide is purified based on the genetic engineering technique or chemical synthesis technique, column chromatography is used. However, because hPHT is a basic peptide, it would be adsorbed to resin constituting a column if it were unscrupulously applied to the column. To prevent the adsorption of hPTH and raise its solubility, an acid is used as an eluent. For a peptide to serve as a material of a pharmaceutical composition, the peptide must be incorporated in a lyophilized composition which will serve as a starting material for preparation of the pharmaceutical composition. To meet this requirement, the acid must be volatile, which limits the range of usable acids.

For illustration, let's assume, for example, hydrochloric acid is used for the present purpose. It is highly acidic even at a low concentration, readily causes accessory reactions such as hydrolysis, and is highly corrosive. Thus, hydrochloric acid is not suitable for the present purpose. If an organic acid is employed for the present purpose, it may be selected from trifluoroacetic acid, formic acid and acetic acid that have a low boiling point. However, it is undesirable to incorporate trifluoriacetic acid in a pharmaceutical composition in terms of safety. Formic acid is also limited in its use because of its reducing activity, and is not compatible with a peptide such as hPTH.

By contrast, acetic acid is the most appropriate to serve as a material for a pharmaceutical composition, on account of its safety and chemical properties, and has been used as an acid indispensable for the final stage purification of a basic peptide. For example, the purification process based on reverse phase high-performance liquid column chromatography (reverse phase HPLC) or on size exclusion column chromatography has been performed using an eluate containing acetic acid with a favorable result. During the process, acetic acid is added at a concentration sufficient to prevent hPTH from being adsorbed to the column, and thus a sample eluated from an aqueous solution of acetic acid, a target peptide fraction, and a lyophilized composition prepared therefrom contain acetic acid at a concentration above the level at which acetic acid exists only as the constituent of a salt of the basic amino acid residues, that is, acetic acid exists not only as the constituent of hPTH salt, but as an adherent attached.

Namely, acetic acid existing in a pharmaceutical component based on hPTH takes two forms: it exists as the constituent of a salt of hPTH, and an adherent attached. Since acetic acid is a volatile substance, it is difficult to keep the content of acetic acid in a lyophilized composition at a constant level, because the content of acetic acid in a lyophilized composition varies depending on the lyophilization condition, the concentration of acetic acid in the original solution prior to lyophilization, with respect to the concentration of hPTH coexistent in the original solution.

The pharmaceutical component of this invention comprises hPTH and acetic acid, in which the content of acetic acid existing as the constituent of a salt of hPTH and an adherent is reduced. This component, because of having a reduced content of acetic acid, improves the stability of hPTH, and ensures a good use feeling when incorporated in a pharmaceutical composition for intranasal administration, and used as such.

In the pharmaceutical component of this invention, acetic acid with a reduced content is defined as acetic acid whose content is reduced below a certain specified chemical equivalent.

Because hPTH(1-34) contains nine basic amino acid residues (including tryptophan residue), one molecule of it can bind with nine molecules of monovalent acid (acetic acid and others) at maximum to form a salt. However, it also contains four acidic amino acid residues which may bind with the basic residues to form a salt within the same molecule. Therefore, with regard to hPTH(1-34) of this invention, the remaining five basic amino acid residues are considered as available for binding with acetic acid, from which the expected weight of acetic acid to bind with one molecule of hPTH(1-34) or a chemical equivalent of acetic acid to hPTH(1-34) is derived. The acetic acid content can be obtained by using the equation I: the weight of acetic acid×100(%)/the weight of human parathyroid hormone peptide, on the weight of acetic acid and human parathyroid hormone peptide. The chemical equivalent of acetic acid to hPTH(1-34) is about 7.3% (weight % unless otherwise stated) as the acetic acid content.

Similarly, since hPTH(1-84) contains 19 basic amino acid residues (including tryptophan) and 12 acidic amino acid residues, in preparing a hPTH(1-84) preparation according to this invention, it is assumed that the seven excess basic amino acid residues are available for binding with acetic acid in one molecule of hPTH(1-84), which will give the expected weight of acetic acid to bind with one molecule of hPTH or a chemical equivalent of acetic acid to hPTH(1-84). The acetic acid content can be obtained by using the equation I, the chemical equivalent of acetic acid to hPTH (1-84) is about 4.5% as the acetic acid content.

Namely, according to this invention, acetic acid contained in an amount less than its chemical equivalent means that of an amount of acetic acid omitted as an adherent, but only as the constituent of a salt of hPTH whose percent weight is below the chemical equivalent.

The present invention provides a stable pharmaceutical component based on hPTH by controlling the content of acetic acid thereof, and a pharmaceutical composition for intranasal administration containing the pharmaceutical component.

Further, the present invention provides a pharmaceutical component based on hPTH in which the content of acetic acid is controlled such that it is kept at a specified level, and a medicinal composition for intranasal administration containing the pharmaceutical component.

Since a peptide is generally unstable in a solution, its lyophilized product is used as a material for a pharmaceutical component. If a peptide such as hPTH which exists as a salt containing acetic acid or a volatile substance as the constituent of the salt, is dissolved in water or in diluted acetic acid, and the lyophilized product thereof is used as a material for preparing a pharmaceutical component, the content of acetic acid in the component will not stay at a constant level, which poses a problem. This invention enables preparation of an aqueous solution of hPTH with a reduced content of acetic acid, thereby enabling the production of an hPTH-based pharmaceutical component consistently containing a specific amount of acetic acid in stable. Thus, this invention is advantageous also from the aspect of manufacturing stability.

For a pharmaceutical component according to this invention, the acetic acid content with respect to the weight of hPTH is kept below the chemical equivalent. For example, for the hPTH(1-34)-based component acetic acid content is kept below about 7.3% with respect to the weight of hPTH(1-34), more preferably about 6.0% or less particularly about 4.0% or less from the view-point of stability and utility, or more preferably about 4.0% or less, particularly about 3.0% or less from the view-point of manufacturing stability. It is not preferable that the content of acetic acid were kept at a too low level from the view-point of manufacturing stability, since the component, although it would give an excellent stability and use feeling, would readily become insoluble at a high pH: hPTH(1-34) has an isoelectric point at 8.2 (pI=8.2). The content of acetic acid is preferably kept at about 0.5% or higher, particularly about 1.0% or higher. On the other hand, for hPTH(1-84)-based component, the acetic acid content is kept below about 4.5%, preferably about 3.0% or less from the view-point of stability and utility, more preferably about 0.1% or higher from the view-point of manufacturing stability.

The pharmaceutical component of this invention can be produced by any publicly known method or by any method equivalent with the former. Namely, reduction of the content of acetic acid existing as the constituent of a salt of hPTH or as an adherent below a specified level can be achieved by appropriately introducing a known method such as dialysis, electrodialysis, ion exchange chromatography, size exclusion column chromatography, reverse phase HPLC, etc., into the purification process of hPTH which has been obtained by a genetic engineering-based technique or a chemical synthesis-based technique.

When the excess content of acetic acid is reduced by a method such as dialysis, electrodialysis, ion exchange chromatography, etc., adjustment of the content of acetic acid to any desired level may be achieved by directly monitoring the pH of the hPTH solution, or the concentration of acetic acid in the solution, so that an hPTH solution containing acetic acid at a desired concentration may be obtained.

For example, adjustment of the acetic acid content in an aqueous solution of hPTH may be achieved based on the relation of the acetic acid content in the solution to the pH of the solution.

Dialysis may occur as follows: an aqueous solution of hPTH which has been prepared by a genetic engineering-based or chemical synthesis-based technique, or the same aqueous solution whose pH has been adjusted to pH5–9, with the addition of an alkaline solution such as an aqueous solution of sodium hydroxide or ammonia is placed in a dialysis membrane in the form of a cylinder which will pass low molecular weight components; the solutes in the solution is subject to dialysis based on simple diffusion; and the acetic acid content is removed by this process. For example, a solution of hPTH(1-34) (acetic acid content being 2%) is obtained by subjecting a starting solution to dialysis until the solution outside the dialysis membrane comes to have a pH of about 6.5.

Electrodialysis may occur as follows: an aqueous solution of hPTH which has been prepared by a genetic engineering-based or chemical synthesis-based technique, or the same aqueous solution whose pH has been adjusted to pH5–9, with the addition of an alkaline solution such as an aqueous solution of sodium hydroxide or ammonia is allowed to circulate between two dialysis membranes exposed to an electric field which will pass components having a molecular weight of 300 or less; and acetic acid ions will migrate to the cathode to accumulate there while free hPTH basic ions will migrate to the anode to accumulate there; and acetic acid ions with a low molecular weight are allowed to pass through the membranes to the outside, while free hPTH basic ions with a large molecular weight are allowed to circulate within the dialysis system. It will be possible to produce a solution of hPTH containing a desired constant amount of acetic acid, by monitoring the pH or ionic strength of dialysis solution, thereby checking the reduced acetic acid content. For example, an hPTH(1-34) solution (acetic acid content being about 2%) will be obtained by applying electrodialysis to a starting solution until the pH of dialysis solution comes to have a pH of about 6.5.

In ion exchange chromatography, acetic acid is adsorbed by binding to a basic ion exchange resin to be removed. For example, an aqueous solution of hPTH which has been prepared by a genetic engineering-based or chemical synthesis-based technique, is applied to a basic ion exchange resin column made of a quaternary or secondary ammonium resin; acetic acid is allowed to be bound to the resin through ion-to-ion binding; and a non-adsorbed fraction simply passing through the column is recovered to give an hPTH solution with a reduced acetic acid content. It is possible to obtain an hPTH solution with a specified acetic acid content by altering the amount of ion exchange resin with respect to the weight of hPTH in the solution. For example, in order to obtain an hPTH(1-34) solution (acetic acid content being about 2%), a resin may be used that has a weight sufficiently large to alter the pH of eluate to about pH6.5.

Size exclusion column chromatography may occur as follows: an aqueous solution of hPTH which has been prepared by a genetic engineering-based or chemical synthesis-based technique, or the same aqueous solution whose pH has been adjusted to pH5–9, with the addition of an alkaline solution such as an aqueous solution of sodium hydroxide or ammonia is applied to a column; an aqueous solution containing an organic solvent such as acetonitrile is used for eluation; and acetic acid is thereby removed. It is possible to obtain an hPTH solution with a specified acetic acid content by altering the pH of the aqueous solution of hPTH to be applied to a column. For example, to obtain an hPTH(1-34) solution (acetic acid content being about 2%), an aqueous solution of hPTH having been so adjusted as to give a pH of about 6.5, is applied to a column, and a fraction consisting of hPTH(1-34) eluate is recovered.

In reverse phase HPLC, an aqueous solution of hPTH which has been prepared by a genetic engineering-based or chemical synthesis-based technique, or the same aqueous solution whose pH has been adjusted to pH5–9, with the addition of an alkaline solution such as an aqueous solution of sodium hydroxide or ammonia is served. The solution is applied to a C18 or C4 column initialized with water; and for example water is used as an eluate to elute inorganic salts. Then, an aqueous solution containing an organic solvent such as acetonitrile is allowed to flow to elute hPTH adsorbed to the column; and an hPTH solution with a reduced acetic acid content is thereby obtained.

It is possible to obtain an hPTH solution with a specified acetic acid content by adjusting the pH of an aqueous solution of hPTH to be applied to a column. It is also possible to obtain an hPTH solution with a specified acetic acid content by preparing an hPTH solution with a too small acetic acid content, for example as low a level as permitted to the method, and then adding a necessary amount of acetic acid to give an hPTH solution with a specified acetic acid content. For example, an hPTH(1-34) solution from which acetic acid has been excessively removed, is diluted with water to 10 mg/mL; acetic acid is added to the solution until the pH of the solution becomes pH6.5; and an hPTH(1-34) solution (acetic acid content being about 2%) is thereby obtained.

An aqueous solution of hPTH obtained by the method as described above is lyophilized by a conventional method to produce a pharmaceutical component of this invention.

The medicinal component of this invention may include water-soluble organic acids, or preferably at least one selected from citric acid, adipic acid and glycolic acid, so as to improve the mucosal absorption of the component. A pharmaceutical component further including such an organic acid will ensure a high stability, and will also ensure an excellent use feeling, when administered through a route other than parenteral routes, or particularly when administered nasally.

Accordingly, the pharmaceutical component of this invention may be used as a component of a pharmaceutical composition for intranasal administration suitable for a long term use.

Moreover, the pharmaceutical composition of this invention for intranasal administration has a property of being compatible with widely varied functional components as well as with a carrier, excipient, viscosity-increasing agent, preserver, stabilizer, anti-oxidant, binder, disintegrant, humectant, lubricant, colorant, flavoring agent, corrigent, suspendmolding agent, emulsifying agent, solubilizer, buffering agent, tonicity agent, detergent, soothing agent, Sulfur-containing reducing agent etc. Thus, the pharmaceutical composition of this invention well tolerates the addition of various functional components which may be introduced to improve absorption, solid stability, etc., as appropriate.

The carrier or excipient may include substances well or sparingly soluble to water such as sugars, polysaccharides, dextrins, celluloses, synthesized or semi-synthesized polymers, amino acids, polyamino acids, proteins, and phospholipids.

The sugars (monosaccharides, oligosaccharides) may include, for example, D-mannitol, glucose, lactose, fructose, inositol, sucrose, maltose, etc., while the polysaccharides may include dextran, pullulan, alginic acid, hyaluronic acid, pectic acid, phytic acid, phytin, etc. The dextrins may include α-cyclodextrin, β-cyclodextrin, γ-cyclodextrin, dextrin, hydroxypropylstarch, hydroxyethylstarch, etc.

The celluloses may include methylcellulose, ethylcellulose, hydroxyethylcellulose, hydroxypropylcellulose, hydroxypropylmethylcellulose, sodium carboxymethylcellulose, etc.

The synthesized or semi-synthesized polymers may include polyvinyl alcohol, carboxyvinyl polymer, polyethylene glycol, polyvinyl pyrrolidone (PVP), sodium polyacrylate, polyactic acid, etc.

The amino acids may include glycine, taurine, while the polyamino acids may include polyglutamic acid, polyaspartic acid, polyglycine, polyleucine, etc.

The proteins may include gelatin and others. In addition, chitin and chitosan may be included.

Of these carriers or excipients, particularly preferred are sucrose, maltose, α-cyclodextrin, β-cyclodestrin, dextrin, D-mannitol, inositol, lactose, dextran, methylcellulose, hydroxypropylcellulose, polyvinyl alcohol, pullulan, etc.

Besides them, sorbic acid; benzalconium chloride; cetylpyridinium chloride; benzethonium chloride; parabens such as methyl paraoxybenzoate, ethyl paraoxybezoate, propyl paraoxybenzoate, butyl paraoxybenzoate, and others; gum acacia; sorbitol; magnesium stearate; talc; silica; microcrystalline cellulose; starch; calcium phosphate; vegetable oil; carboxymethylcellulose; sodium lauryl sulfate; water; ethanol; glycerin; and syrup.

Typical examples of surfactants are listed below. Among these, single or combination of more than two of these surfactants can be added to the formulation in the invention.

Nonionic surfactants may include sorbitan esters of fatty acids, for example, sorbitan monocaprilate, sorbitan monolaurate, sorbitan monopalmitate, etc, and glycerol esters of fatty acids, for example, glyceryl monocaprilate, glyceryl monomyristate, glyceryl monostearate, etc, and polyglycerol esters of fatty acids, for example, decaglyceryl monostearate, decaglyceryl distearate, decaglyceryl monolinoleate, etc, and polyoxyethylene sorbitan esters of fatty acids, for example, polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate, etc, and polyoxyethylene sobitol esters of fatty acids, for example, polyoxyethylene sobitol tetrastearate, polyoxyethylene sobitol tetralaurate, etc, and polyoxyethylene glycerol esters of fatty acids such as polyoxyethylene glyceryl monostearate, and polyethylene glycerol esters of fatty acids such as polyethylene glyceryl distearate, and polyoxyethylene alkyl ether such as polyoxyethylene lauryl ether, and polyoxyethylene polyoxypropylene alkyl ether, for example, polyoxyethylene polyoxypropylene glycol ether, polyoxyethylene polyoxypropylene propylether, polyoxyethylene polyoxypropylene cetyl ether, etc, and polyoxyethylene alkylphenyl ether such as polyoxyethylene nonylphenyl ether, and polyoxyethylene caster oils, for example, polyoxyethylene caster oil, polyoxyethylene hydrogenated caster oil, and polyoxyethylene yellow beeswax derivatives such as polyoxyethylene sorbitol yellow beeswax, and polyoxyethylene lanolin derivatives such as polyoxyethylene lanolin, and polyoxyethylene amide of fatty acids with HLB 6 to 18 such as polyoxyethylene stearylamide.

Anionic surfactants may include alkyl sulfate ($C_{10}$ to $C_{18}$) salts, for example, sodium cetyl sulfate, sodium lauryl sulfate, sodium oleylsulfate, etc, and polyoxyethylene alkylether sulfate salts whose average moles of added ethyleneoxide is 2 to 4 and carbons of alkyl groups is 10 to 18, such as sodium polyoxyethylene lauryl ether sulfate, and alkyl sulfo succinate ester salts whose length of alkyl groups is 8 to 18 such as sodium lauryl sulfo succinic acid ester.

Naturally occurring sulfactants may include lecithin, and glycerol lipid phosphate, and sphingolipids such as sphingomyelin, and sucrose esters of fatty acids ($C_{12}$ to $C_{18}$).

Sulfur-containing reducing agents may include N-acety cysteine, N-acety homocysteine, thioctic acid, thioethanol, thioethanolamine, thioglycerol, thiosorbitol, thioglycolic acid and its salts, sodium thiosulfate, glutathione, thioalkanic acids ($C_1$ to $C_7$) having sulfhydryl group.

Anti-oxidants may include erysorbic acid, dibutylhydroxytoluene, butylhydroxyanisole, alpha-tocopherol, tocopherol acetate, L-ascorbic acid and its salts, L-ascorbyl palmitate, L-ascorbyl stearate, sodium bisulfite, sodium sulfite, triamyl gallate, propyl gallate, and chelating agents, for example, calcium disodium edetate (EDTA), sodium pyrophospate, sodium metaphosphate, etc.

For a pharmaceuticl composition of this invention, hPTH may exist at about 0.01–20%, preferably at about 0.05–10%, and an organic acid may be added as appropriate. The content of the latter prior to use is about 0.05–99.5%, preferably about 0.1–99.0%. A carrier or excipient which is usually added during preparation of a medicinal product may be added as appropriate, or may exist, for example, at about 0.01–99.5% prior to use. Other various functional components may be added as appropriate, or may exist, for example, at about 0.05–99.5% prior to use.

Preparation of the pharmaceutical composition for intranasal administration of this invention may be achieved by any known method.

For example, an hPTH-based pharamceutical component in which the acetic acid content has been reduced may be served as a pharmaceutical composition. Alternatively, to an hPTH-based pharmaceutical component in which the acetic acid content has been reduced, may be added as appropriate a carrier or excipient which is usually added during preparation of a pharmaceutical product, and an organic acid and other various functional components, and the resulting compound may be used as a pharmaceutical component. Addition of an organic acid may take place to replace acetic acid, or simply for addition. For example, an hPTH pharmaceutical component to which are added as appropriate a carrier or excipient which is usually added during preparation of a pharmaceutical preparation, an organic acid, and various functional components; a resulting mixture is dissolved for one time in distilled water; the solution is lyophilized; and a uniform composition is thereby obtained.

Alternatively, an hPTH pharmaceutical component, and a carrier or excipient which is usually used during preparation of a pharmaceutical preparation are dissolved for one time in distilled water; an organic acid and various functional components are then added to the solution; the resultant solution is lyophilized; and a uniform composition is thereby obtained. As a further variant, an hPTH pharmaceutical component, an organic acid, and various functional components are dissolved for one time in distilled water; the solution is lyophilized; a desired amount of the lyophilized compound is dissolved as needed in combination with a carrier or excipient which is usually used during preparation of a pharmaceutical preparation; and a uniform composition is thereby obtained.

The pharmaceutical component of this invention may take various dosage forms depending on its expected administration routes: it may take a form appropriate for being applied to the mucosa of the rectum, nasal cavity, oral cavity, etc. The pharmaceutical composition for intranasal administration of this invention is preferably applied in a form appropriate for intranasal use.

A preferred example of the pharmaceutical composition for intranasal administration of this invention may occur as an on-demand dissolvable form of which a lyophilized portion contains a pharmaceutical composition of this invention provided lyophilized and a dissolving solution portion is attached to the former.

An organic acid such as citric acid, adipic acid or glycolic acid which is added for promoting absorption may exist as the constituent of a salt of hPTH, an adherent, or an additive. Alternatively, the organic acid may be dissolved in the dissolving solution portion.

Administration of a pharmaceutical composition for intranasal administration of this invention may be achieved by any known method. For example, spraying a pharmaceutical composition for intranasal administration of this invention is applicable: the composition may be placed in a container; a nebulizer is attached to the container; the tip of nozzle is inserted into the nasal cavity; and the pharmaceutical composition is sprayed.

The dose of a pharmaceutical composition of this invention may vary depending on the kind of disease, the age and weight of the patient, the severity of disease, and the route through which the composition is administered. If, for example, an hPTH-based composition is applied nasally, it may be applied once daily or several times daily with each dose reduced in proportion, successively for a period. A single dose of hPTH(1-34)-based composition preferably occurs in the range of 10–5,000 μg. During treatment, a so-called wash-out may be inserted, and treatment may then be resumed.

EXAMPLE

The present invention will be detailed below by means of Examples, but this invention should not be limited to those examples.

The testing methods and apparatuses used in Examples are based on what is described below, unless otherwise stated.

1. Analysis of hPTH by HPLC

Determination of the content of a studied peptide in a composition, and checking whether any decomposition products (by-products) are present in the composition was achieved by reverse phase HPLC using the apparatuses and conditions specified below.
Apparatus: LC-9A system from Shimadzu Ltd.
Column: YMC Protein-RP (4.6 mmø×150 mm)
Column temperature: 40° C.
Eluate: the concentration of acetonitrile in 0.1% trifluoroacetic acid is linearly varied from 25% to 40% in 30 minutes.
Flow rate: 1 mL/min
Detection: UV(210 nm)
Injection amount: 50 μL 2. Analysis of Acetic Acid The contents of acetic acid of dialysis solutions and of lyophilized compositions were determined by ion exchange chromatography under the conditions as specified below.
Apparatus: LC-91 system from Shimadzu Ltd.
Column: IC-A1 from Shimadzu (4.6 mmø×100 mm)
Column temperature: 40° C.
Eluate: 1:1 mixture of 0.84% aqueous solution of phthalic acid and 0.58% aqueous solution of tris hydroxymethyl aminomethane
Flow rate: 1.5 mL/min
Detection: electric conductivity detector
Injection amount: 10 μL 3. Mass Analysis Determination of the masses of hPTH, decomposition products (by-products) of hPTH, and their enzymatic digests was achieved with the apparatuses under conditions as specified below.
Apparatus: MAT TSQMS from Finnigan
Ion source: ESI
Detection mode: positive
Spray voltage: 4.5 kV
Capillary temperature: 250° C.
Mobile phase: (1:1) mixture of 0.2% acetic acid and methanol
Flow rate: 0.2 mL/min
Scan range: m/z 550–850

4. Sequencing Amino Acids

Determination of the amino acid sequences of decomposition products (by-products) of hPTH and their enzymatic digests was achieved with the following apparatuses.
Apparatus: type 477A sequencer from PerkinElmer 5. Determination of Amino Acid Composition Determination of the amino acid compositions of hPTH, decomposition products (by-products) of hPTH, and their enzymatic digests was achieved with the following apparatuses.
Apparatus: type L-8500 amino acid analyzer from Hitachi 6. Storage of Specimens (Stability Test)

The test specimens were stored in a depository kept under the conditions as specified below.
Apparatus: LH-30-14 from Nagano Science Co. Ltd.
Temperatures set: 1) 40±1° C., 2) 60+1° C., 3) 80±2° C.

7. Lyophilization

Apparatus: RL-903BS from Kyowa Vacuum Engineering, Ltd.
Vial: 15 mL glass vial

Reference Example 1

Production of hPTH(1-34) (1)

The expression plasmid pG117S4HPPH34 (Japanese Patent Laid-Open No. 9-29660) containing a gene coding for a chimera protein of hPTH(1-34) obtained by connecting a DNA fragment coding for a derivative of β-galactosidase derived from *E. coli* with a DNA fragment coding for hPTH(1-34) through the intervention of a DNA fragment coding for a linker containing a cleavage motive (Lys-Arg) of Kex2 protease or a processing enzyme, was introduced into the cells of M25 strain *E. coli* (w3110/ompT: Sugimura et al., Biochem. Biophys. Res. Commun., vol. 153, 1988, p. 753–759). The transformed cells of M25 strain *E. coli* were cultivated on a medium containing 2% yeast extract in a 20 L culture tank.

The cultivation was continued until the density of cells became $OD_{660}$=12. The recovered cells were broken to pieces with a high pressure homogenizer (Manton-Gaullin) in 10 mM Tris-HCl buffer (pH8.2) supplemented with 1 mM EDTA, centrifuged, and washed, to produce about 625 mL of suspension containing about 100 g of inclusion bodies filled with the chimera protein. To 250 mL of suspension containing 40 g of inclusion bodies, were added 100 mL of 1M Tris-HCl buffer (pH8.2), 50 mL of 5M NaCl, 500 mL of deionized water, and 900 g of urea, and the mixture was agitated at 30° C. to allow the inclusion bodies to dissolve.

The solution was diluted with deionized water to 5 L, to which was added 50 mL of 250 mM $CaCl_2$. Then, to the solution was added Kex2-660 comprising amino acid residues designated an amino acid Nos. 1–660 (Japanese Patent Laid-Open No. 10-229884) which is a derivative from Kex2 protease, until it existed at 20 kU/mL or higher. The mixture was gently stirred for two hours, and hPTH(1-34) was cleaved from the chimera protein. The reaction solution was adjusted to pH6.4 with addition of acetic acid; it was then diluted two fold with deionized water, thereby allowing the chimera protein and β-galactosidase derivative remaining unreacted to precipitate; and the yield was centrifuged to give a supernatant containing 6.7 g of hPTH(1-34). The supernatant was adjusted to pH5.0 with addition of acetic acid; the solution was applied to a cation exchange resin (SP Toyopearl from Tosoh Corporation) previously equilibrated with 10 mM sodium acetate to allow hPTH(1-34) to be adsorbed to the resin; the resin was washed with 10 mM sodium acetate buffer; and 0.4M NaCl was used to give a fraction containing 6.0 g of hPTH(1-34).

To this fraction was added acetic acid to 3 v/v %; the solution was applied to a column for low pressure reverse phase ODS (Soken ODS-W from Soken Chemicals Co.) previously equilibrated with 3 v/v % acetic acid; and 30 v/v % acetonitrile containing 3 v/v % acetic acid was used to eluate hPTH(1-34). The eluate containing hPTH(1-34) was enriched under a reduced pressure; the yield was applied to a column for reverse phase HPLC (TSKgel0DS120T with a size of 55 mm×600 mm from Tosoh Corp.); and solution of acetonitrile in 5 v/v % acetic acid was allowed to flow at 40 mL/min for 60 minutes with the concentration of acetonitrile being linearly varied from 16% to 32% in the mean time, to eluate hPTH(1-34). Thus, a purified fraction containing 4 g of hPTH(1-34) was obtained.

A 60 g of the remaining inclusion bodies was similarly treated, and another purified fraction containing 5 g of hPTH(1-34) obtained therefrom was combined with the former; the mixture was removed of acetonitrile under a reduced pressure; and the yield was diluted with 5 v/v % acetic acid such that the concentration of hPTH(1-34) fell to 10 mg/mL. A 15 ml of the solution was placed in each glass vial; and all the vials containing the solution were lyophilized to give 9 g of hPTH(1-34) in total (150 mg×60 vials).

ESI-MS: 4117.7 (theoretical value being 4117.8). Amino acid composition after being hydrolyzed with 6N hydrochloric acid: Asx-4.0(4); Ser-2.6(3); Glx-4.9(5); Gly-1.0(1); Val-3.0(3); Met-2.0(2); Ile-1.0(1); Leu-5; Phe-1.1(1); Lys-30(3); His-3.0(3); Arg-2.0(2); and Trp-not detected (1).

Reference Example 2

Production of hPTH(1-34) (2)

Similar live microbes to those used in Reference Example 1 were cultivated in a 200 L culture tank. The cultivation was continued until the density of cells became $OD_{660}$=160. The recovered cells were broken to pieces with a high pressure homogenizer in 10 mM Tris-HCl buffer (pH8.2) supplemented with 1 mM EDTA, centrifuged, and washed, to produce about 10 L of suspension containing about 5 kg of inclusion bodies filled with the chimera protein.

To 4.0 L of suspension containing 2 kg of inclusion bodies, were added 1.6 L of 1M Tris-HCl buffer (pH8.2), 0.8 L of 5M NaCl, 15 L of deionized water, and 13 kg of urea, and the mixture was agitated at 30° C. to allow the inclusion bodies to dissolve.

The solution was diluted with deionized water to 80 L, to which was added 0.8 mL of 250 mM $CaCl_2$. Then, to the solution was added Kex2-660 (Japanese Patent Laid-Open No. 10-229884), until it existed at 10 kU/mL or higher. The mixture was gently agitated for one hour, and hPTH(1-34) was separated by cleavage from the chimera protein. The reaction solution was adjusted to pH6.3 with addition of acetic acid; it was then diluted two fold with deionized water, thereby allowing the chimera protein and β-galactosidase derivative remaining unreacted to precipitate; and the yield was subjected to pressurized filtration to give a supernatant containing hPTH(1-34).

The supernatant was adjusted to pH5.0 with addition of acetic acid; the solution was applied to a cation exchange resin column (5 L)(Poros 50HS from PerSeptive Biosystems, USA) previously equilibrated with 10 mM sodium acetate buffer to allow hPTH(1-34) to be adsorbed to the column; the column was washed with 10 mM sodium acetate buffer; and 0.4M NaCl with a concentration gradient was used to give a fraction containing hPTH(1-34). To this fraction was added acetic acid to 3 v/v %; the solution was applied to a column (5 L) for low pressure reverse phase ODS (Soken ODS-W from Soken Chemicals Co.) previously equilibrated with 3 v/v % acetic acid; and 30 v/v % acetonitrile containing 3 v/v % acetic acid was used to eluate hPTH(1-34).

The eluate containing hPTH(1-34) was enriched under a reduced pressure; the yield was filtrated through a 0.22 μm filter; the filtrate was applied to a column for reverse phase HPLC (TSK ODS 80Ts 20 μm, 105 mmID×550 mm from Tosoh Corp.); and acetonitirile with a concentration gradient was used in the presence of 3 v/v % acetic acid to eluate hPTH(1-34). Several eluates thus obtained were combined; and the solution was removed of acetonitrile through distillation under a reduced pressure, to give 10.4 L of conc. hPTH(1-34) solution containing 70 g of hPTH(1-34) at 99.6%. Out of 3 kg of the remaining inclusion bodies, 2 kg was subjected to the same purification process, to give 11.6 L of conc. hPTH(1-34) solution containing hPTH(1-34) at 99.6%.

Reference Example 3

Production of hPTH(1-84)

The expression plasmid pGP#19 (Japanese Patent Laid-Open No. 9-29660) containing a gene coding for a chimera protein of hPTH(1-84) obtained by connecting a DNA fragment coding for a derivative of β-galactosidase derived from *E. coli* with a DNA fragment coding for hPTH(1-84) through the intervention of a DNA fragment coding for a linker containing a cleavage motive (Lys-Arg) of Kex2 protease or a processing enzyme, was introduced into the cells of M25 strain *E. coli*. The transformed cells of M25 strain *E. coli* were cultivated at 37° C. in a 3 L culture tank. The cultivation was continued until the turbidity ($OD_{660}$) of culture solution became $OD_{660}$=1. Then, isopropyl beta-thiogalactoside (IPTG) was added to 1.0 mM.

The cultivation was further continued for four hours. The cells were recovered by centrifugation; and the cells were then suspended in TE (10 mM Tris and 1 mM EDTA at pH8.0). The cells were broken to pieces with a French press, subjected to a repetition of centrifugation and resuspension, and washed, to produce inclusion bodies. A suspension of the inclusion bodies was added for dissolution to a solution (pH8.0) containing 8.0M urea and 10 mM Tris, and centrifuged; the supernatant was loaded onto a Toyopearl column (Toso Corp.); and NaCl with a concentration gradient of 0–0.4M was used to eluate enriched hPTH(1-84). The inclusion body dissolving enriched solution was further concentrated by ultrafiltration with a removal limit of 10,000 MW. The yield was diluted to give a solution in which the constituents became 50 mM for BisTris at pH6.8, 1.0 mM for $CaCl_2$, and 5 mg/mL for the chimera protein. Kex2-660 was added to 2 kU/mL, and reaction was allowed to proceed at 30° C. for one hour to separate hPTH(1-84) by cleavage.

The reaction solution was adjusted to pH5.0 with addition of acetic acid; it was then diluted two fold with deionized water, thereby allowing the chimera protein and β-galactosidase derivative remaining unreacted to precipitate; and the yield was centrifuged to give a supernatant containing hPTH(1-84). To the supernatant was added acetic acid to 3 v/v %; and the solution was applied to TSK gel ODS 80Ts (21 mmID×250 mm, Tosoh Corporation) previously equilibrated with 3 v/v % acetic acid for purification. Fractions containing 98% or higher hPTH(1-84) were combined; the resulting solution was removed of solvent; and the residue was lyophilized to give 500 mg of hPTH(1-84). The molecular weight and amino acid composition of this substance are as indicated below. Based on those data, the substance was identified as hPTH(1-84).

ESI-MS: 9424.7 (theoretical value being 9424.7). Amino acid composition after being hydrolyzed with 6N hydrochloric acid: Asx-10.1(10); Thr-1.1(1); Ser-6.3(7); Glx-11.0 (11); Pro-2.9(3); Gly-4.1(4); Ala-7.0(7); Val-8.0(8); Met-1.9 (2); Ile-1.0(1); Leu-10; Phe-1.0(1); Lys-8.9(9); His-3.9(4); Arg-5.0(5); and Trp-not detected (1).

Example 1

Removal of Acetic Acid from hPTH(1-34) (1)

(1) An amount of preparation corresponding to 150 mg as hPTH(1-34) obtained in Reference Example 1 was dissolved in distilled water (30 mL), to give an aqueous solution (pH4.7) of hPTH(1-34) at 5 mg/mL. This solution was dialyzed against distilled water (100 mL) with a GI micro acilyzer (Asahi Kasei Corp.) incorporating an electrodialysis membrane AC-130-10 (Asahi Kasei Corp.). The dialysis was continued for removal of acetic acid until the pH of the dialysis solution became pH5.0. The enriched solution containing 6.8% acetic acid was lyophilized, and dried mass corresponding to about 150 mg as hPTH(1-34) was obtained as acetic acid content being 4.8%.

(2) An amount of preparation corresponding to 150 mg as hPTH(1-34) obtained in Reference Example 1 was dissolved in distilled water (30 mL), to give an aqueous solution (pH4.7) of hPTH(1-34) at 5 mg/mL. This solution was subjected to electrodialysis as in Example (1): the dialysis was continued for removal of acetic acid until the pH of the dialysis solution became pH5.5. The enriched solution containing 4.6% acetic acid was lyophilized, and dried mass corresponding to about 150 mg as hPTH(1-34) was obtained as acetic acid content being 3.8%.

(3) An amount of preparation corresponding to 150 mg as hPTH(1-34) obtained in Reference Example 1 was dissolved in distilled water (30 mL), to give an aqueous solution (pH4.7) of hPTH(1-34) at 5 mg/mL. This solution was subjected to electrodialysis as in Example (1): the dialysis was continued for removal of acetic acid until the pH of the dialysis solution became pH5.9. The enriched solution containing 3.1% acetic acid was lyophilized, and dried mass corresponding to about 150 mg as hPTH(1-34) was obtained as acetic acid content being 2.9%.

(4) An amount of preparation corresponding to 150 mg as hPTH(1-34) obtained in Reference Example 1 was dissolved in distilled water (30 mL), to give an aqueous solution (pH4.7) of hPTH(1-34) at 5 mg/mL. This solution was subjected to electrodialysis as in Example (1): the dialysis was continued for removal of acetic acid until the pH of the dialysis solution became pH7.0. The enriched solution containing 1.6% acetic acid was lyophilized, and dried mass corresponding to about 150 mg as hPTH(1-34) was obtained as acetic acid content being 1.6%.

From above results it was demonstrated that with the reduction of acetic acid content, the decrement of acetic acid content by lyophilization becomes smaller, and that with the reduction of acetic acid content, the fractional decrement of acetic acid content becomes smaller. Accordingly, reduction of the content of acetic acid in an hPTH component is useful for preparing a pharmaceutical hPTH component containing a specified amount of acetic acid, which has been difficult to obtain by conventional techniques.

Example 2

Removal of Acetic Acid from hPTH(1-34) (2)

To a solution containing preparation corresponding to about 150 mg as hPTH(1-34) obtained in Reference Example 2 was added 5N NaOH to pH5.5. One fourth of the solution was loaded onto a column for low pressure reverse phase ODS (Soken ODS-W (800 mL) from Soken Chemicals Co.) previously equilibrated with 5 v/v % aqueous solution of acetonitrile, to allow hPTH(1-34) to be adsorbed to the column. A 4 L of 5 v/v % aqueous solution of acetonitrile was flowed to eluate sodium acetate; and 50 v/v % aqueous solution of acetonitrile was then flowed to eluate hPTH(1-34). This process was repeated for each of the four parts; the hPTH(1-34) rich fractions of the four parts were combined to give 8.2 L of nearly acetic acid free fraction containing 122.5 g of PTH(1-34) was obtained (1.13% acetic acid content to hPTH(1-34)).

To this fraction was added distilled water to give an hPTH(1-34) solution at 10 mg/mL; to this solution was added 2.3 g of acetic acid such that the resulting solution contains 122.5 g of PTH(1-34) with 3% acetic acid content at 3%; and the mixture was well stirred. The solution was distributed to vials such that each vial contains 150 mg of hPTH(1-34); and the hPTH(1-34) solution in vial was lyophilized, which gave hPTH(1-34) as acetic acid content being 2.1%.

Example 3

Removal of Acetic Acid from hPTH(1-34) (3)

(1) An amount of preparation corresponding to 300 mg as hPTH(1-34) obtained in Reference Example 1 was dissolved in distilled water (30 mL), to give an aqueous solution of hPTH(1-34) at 10 mg/mL. This solution (pH4.7) containing 9.5% acetic acid was placed in three glass vials, 2 mL for each vial; and they were placed in an FZ-6 lyophilizer (Laboconco Corp.) whose internal pressure was kept at 0.13 mBar or lower; and they were subjected to primary drying (−20° C. in terms of the temperature of the shelf on which they rested for 12 hours) and secondary drying (25° C. at the shelf for 48 hours) for lyophilization. On completion of the secondary drying, the chamber used for lyophilization was filled with nitrogen gas; and the vials were automatically capped. A 2 mL of distilled water was introduced into each vial, and the solution was determined by ion exchange HPLC of its content of acetic acid. The results are shown in Table 1.

(2) An amount of preparation corresponding to 300 mg as hPTH(1-34) obtained in Reference Example 1 was dissolved in distilled water (30 mL), to give an aqueous solution of hPTH(1-34) at 10 mg/mL. This solution (pH4.7) was subjected to electrodialysis using a micro acilyzer (Asahi Kasei Corp.) incorporating an electrodialysis membrane AC-130-10 (Asahi Kasei Corp.). The dialysis was continued for removal of acetic acid until the pH of the dialysis solution became pH5.0 (the content of acetic acid of the solution subject to dialysis being 7.3%). The acetic acid-removed solution was placed in three glass vials, 2 mL for each vial; they were lyophilized as in Example (1); and the content of acetic acid in each sample was determined by ion exchange HPLC. The results are shown in Table 1.

(3) An amount of preparation corresponding to 300 mg as hPTH(1-34) obtained in Reference Example 1 was dissolved in distilled water (30 mL), to give an aqueous solution of hPTH(1-34) at 10 mg/mL. This solution (pH4.7) was subjected to electrodialysis using a micro acilyzer (Asahi Kasei Corp.) incorporating an electrodialysis membrane AC-130-10 (Asahi Kasei Corp.). The dialysis was continued for removal of acetic acid until the pH of the dialysis solution became pH5.5 (the content of acetic acid of the solution subject to dialysis being 4.6%). The acetic acid-removed solution was placed in three glass vials, 2 mL for each vial; they were lyophilized as in Example (1); and the content of acetic acid in each sample was determined by ion exchange HPLC. The results are shown in Table 1.

(4) An amount of preparation corresponding to 300 mg as hPTH(1-34) obtained in Reference Example 1 was dissolved in distilled water (30 mL), to give an aqueous solution of hPTH(1-34) at 10 mg/mL. This solution (pH4.7) was subjected to electrodialysis using a micro acilyzer (Asahi Kasei Corp.) incorporating an electrodialysis membrane AC-130-10 (Asahi Kasei Corp.). The dialysis was continued for removal of acetic acid until the pH of the dialysis solution became pH6.3 (the content of acetic acid of the solution subject to dialysis being 2.0%). The acetic acid-removed solution was placed in three glass vials, 2 mL for each vial; they were lyophilized as in Example (1); and the content of acetic acid in each sample was determined by ion exchange HPLC. The results are shown in Table 1.

(5) An amount of preparation corresponding to 300 mg as hPTH(1-34) obtained in Reference Example 1 was dissolved in distilled water (30 mL), to give an aqueous solution of hPTH(1-34) at 10 mg/mL. This solution (pH4.7) was subjected to electrodialysis using a micro acilyzer (Asahi Kasei Corp.) incorporating an electrodialysis membrane AC-130-10 (Asahi Kasei Corp.). The dialysis was continued for removal of acetic acid until the pH of the dialysis solution became pH7.0 (the content of acetic acid of the solution subject to dialysis being 1.1%). The acetic acid-removed solution was placed in three glass vials, 2 mL for each vial; they were lyophilized as in Example (1); and the content of acetic acid in each sample was determined by ion exchange HPLC. The results are shown in Table 1.

(6) An amount of preparation corresponding to 300 mg as hPTH(1-34) obtained in Reference Example 1 was dissolved in distilled water (30 mL), to give an aqueous solution of hPTH(1-34) at 10 mg/mL. This solution (pH4.7) was subjected to electrodialysis using a micro acilyzer (Asahi Kasei Corp.) incorporating an electrodialysis membrane AC-130-10 (Asahi Kasei Corp.). The dialysis was continued for removal of acetic acid until the pH of the dialysis solution became pH7.6 (the content of acetic acid of the solution subject to dialysis being 0.5%). The acetic acid-removed solution was placed in three glass vials, 2 mL for each vial; they were lyophilized as in Example (1); and the content of acetic acid in each sample was determined by ion exchange HPLC. The results are shown in Table 1.

As is obvious from Table 1, with the reduction of acetic acid content of a sample prior to lyophilization, the decrement of acetic acid content by lyophilization becomes smaller, and that with the reduction of acetic acid contents of samples prior to lyophilization, the variation in acetic acid content among the samples or lots after lyophilization becomes smaller. Accordingly, hPTH with low acetic acid content is demonstrated to be useful for preparing a pharmaceutical hPTH component containing a specified amount of acetic acid, which has been difficult to obtain by conventional techniques.

TABLE 1

Change of acetic acid contents as a result of lyophilization

| Dialysis solution pH | Acetic acid content before lyophilization (%) | Acetic acid content after lyophilization (%) | Average (%) | Difference of acetic acid contents before and after lyophilization (%) |
|---|---|---|---|---|
| 4.7 | 9.5 | 6.7 | 6.6 | 2.9 |
|  |  | 6.5 |  |  |
|  |  | 6.6 |  |  |
| 5.0 | 7.3 | 5.5 | 5.5 | 1.8 |
|  |  | 5.4 |  |  |
|  |  | 5.5 |  |  |
| 5.5 | 4.6 | 4.9 | 4.9 | −0.3 |
|  |  | 4.9 |  |  |
|  |  | 4.8 |  |  |
| 6.3 | 2.0 | 2.1 | 2.1 | −0.1 |
|  |  | 2.1 |  |  |
|  |  | 2.1 |  |  |
| 7.0 | 1.1 | 0.8 | 0.8 | 0.3 |
|  |  | 0.8 |  |  |
|  |  | 0.8 |  |  |
| 7.6 | 0.5 | 0.4 | 0.4 | 0.1 |
|  |  | 0.4 |  |  |
|  |  | 0.5 |  |  |

Example 4

Removal of Acetic Acid from hPTH(1-34)

(1) Similar live microbes to those used in Reference Example 1 were cultivated in a 200 L culture tank. The cells were broken to pieces, centrifuged, and washed; and 4.8 kg of inclusion bodies filled with a chimera protein was obtained. A 2.4 kg out of this was subjected to digestion by Kex2-660 as in Reference Example 2 to obtain hPTH(1-34). The yield was then subjected to purification by cation exchange chromatography, desaltation by reverse phase ODS chromatography, and final purification by reverse phase HPLC. Then, as in Example 2, to the purified fraction was added 5N sodium hydroxide to pH5.5; and the solution was loaded onto a low pressure reverse phase ODS column. A 5 v/v % aqueous solution of acetonitrile was passed to remove sodium acetate; and 50 v/v % aqueous solution of acetonitrile was then flowed to eluate hPTH(1-34). Thus, 5.4 L of solution containing 58 g of PTH(1-34) was obtained (1.2% acetic acid content to hPTH1(1-34). To this solution was added 1.0 g of acetic acid such that the resulting solution contains 58 g of PTH(1-34) with 3% acetic acid content; and the mixture was well stirred. The solution was distributed to vials such that each vial contains 150 mg of hPTH(1-34);

and all the hPTH(1-34) solutions in vial were lyophilized, which gave 57.8 g of hPTH(1-34) as acetic acid content being 2.5% (385 vials).

(2) An amount of preparation corresponding to 150 mg as hPTH(1-34) obtained in Example (1) was dissolved in 3 mL of trifluoroethanol; and 30 mL of diethylether was added for precipitation. A powder obtained therefrom was subjected to drying for 24 hours under a reduced pressure in a desiccator in the presence of sodium hydroxide pellets, to give 130 mg of hPTH(1-34) as acetic acid content being 2.0%.

(3) Into the vial containing preparation corresponding to 150 mg as hPTH(1-34) obtained in Example (1) was introduced 1.53 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 3.6%.

(4) Into the vial containing preparation corresponding to 150 mg as hPTH(1-34) obtained in Example (1) was introduced 3.78 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 5.1%.

(5) Into the vial containing preparation corresponding to 150 mg as hPTH(1-34) obtained in Example (1) was introduced 5.28 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 6.2%.

Reference Example 4

(1) Into the vial containing preparation corresponding to 150 mg as hPTH(1-34) obtained in Example 4(1) was introduced 7.23 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 7.5%.

(2) Into the vial containing preparation corresponding to 150 mg as hPTH(1-34) obtained in Example 4(1) was introduced 9.48 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 9.1%.

(3) Into the vial containing preparation corresponding to 150 mg as hPTH(1-34) obtained in Example 4(1) was introduced 10.53 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 7.5%.

(4) Into the vial containing preparation corresponding to 150 mg as hPTH(1-34) obtained in Example 4(1) was introduced 14.28 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 12.5%.

(5) Into the vial containing preparation corresponding to 150 mg as hPTH(1-34) obtained in Example 4(1) was introduced 16 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 13.7%.

(6) Into the vial containing preparation corresponding to 150 mg as hPTH(1-34) obtained in Example 4(1) was introduced 22.6 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 18.3%.

(7) Into the vial containing preparation corresponding to 150 mg as hPTH(1-34) obtained in Example 4(1) was introduced 100 µL of acetic acid along the internal wall of the vial with a micro-syringe while care being taken not to contact it with hPTH(1-34). Vaporization of acetic acid was performed by placing the vial at 80° C. for five minutes; the vial was agitated with a vortex mixer; and hPTH(1-34) in the vial was turned into fine powder, to give an hPTH(1-34) preparation as acetic acid content being 72.5%.

Example 5

Removal of Acetic Acid from hPTH(1-84)

(1) An amount of preparation corresponding to 50 mg as hPTH(1-84) obtained as acetic acid content being 5.4% in Reference Example 3 was dissolved in distilled water (10 mL). To give an aqueous solution (pH4.7) of hPTH(1-84) at 5 mg/mL. This solution was dialyzed at room temperature against distilled water (100 mL) with a GI micro acilyzer (Asahi Kasei Corp.) incorporating an electrodialysis membrane AC-130-10 (Asahi Kasei Corp.). The dialysis was continued for removal of acetic acid until the pH of the dialysis solution became pH5.0. The enriched solution was lyophilized, and preparation corresponding to about 50 mg as hPTH(1-84) was obtained as acetic acid content being 3.9%.

(2) An amount of preparation corresponding to 50 mg as hPTH(1-84) obtained as acetic acid content being 5.4% in Reference Example 3 was dissolved in distilled water (10 mL), to give an aqueous solution (pH4.7) of hPTH(1-84) at 5 mg/mL. This solution was subject to electrodialysis in the same manner as in Example.(1). The dialysis was continued for removal of acetic acid until the pH of the dialysis solution became pH6.0. The enriched solution was lyophilized, and preparation corresponding to about 50 mg as hPTH(1-84) was obtained as acetic acid content being 2.5%.

(3) An amount of preparation corresponding to 50 mg as hPTH(1-84) obtained as acetic acid content being 5.4% in Reference Example 3 was dissolved in distilled water (10 mL), to give an aqueous solution (pH4.7) of hPTH(1-84) at 5 mg/mL. This solution was subjected to electrodialysis in the same manner as in Example (1). The dialysis was continued for removal of acetic acid until the pH of the dialysis solution became pH7.0. The enriched solution was lyophilized, and preparation corresponding to about 50 mg as hPTH(1-84) was obtained as acetic acid content being 1.3%.

(4) An amount of preparation corresponding to 50 mg as hPTH(1-84) obtained as acetic acid content being 5.4% in Reference Example 3 was dissolved in distilled water (10 mL), to give an aqueous solution (pH4.7) of hPTH(1-84) at 5 mg/mL. This solution was subjected to electrodialysis in the same manner as in Example (1). The dialysis was continued for removal of acetic acid until the pH of the dialysis solution became pH8.0. The enriched solution was lyophilized, and preparation corresponding to about 50 mg as hPTH(1-84) was obtained as acetic acid content being 0.9%.

Example 6

Removal of Acetic Acid from hPTH(1-84) (2)

(1) An amount of preparation corresponding to 100 mg as hPTH(1-84) obtained as acetic acid content being 5.4% in Reference Example 3 was dissolved in 500 µL of trifluoroethanol; and 20 mL of diethylether was added for precipitation. The precipitate was recovered by filtration; and the yield was subjected to drying for 24 hours under a reduced pressure in a desiccator in the presence of sodium hydroxide pellets, to give dried mass corresponding to about 90 mg as hPTH(1-84) obtained as acetic acid content being 1.6%.

(2) A 5.49 mg of dried mass obtained in Example 6(1) was precisely weighed and placed in a 5 mL vial; and 0.3 µL of 10 vol % acetic acid/methylene chloride was added with a micro-syringe, to give preparation as acetic acid content being 2.2%.

(3) A 5.58 mg of dried mass obtained in Example 6(1) was precisely weighed and placed in a 5 mL vial; and 0.6 µL of 10 vol % acetic acid/methylene chloride was added with a micro-syringe, to give preparation as acetic acid content being 2.7%.

(4) A 4.96 mg of dried mass obtained in Example 6(1) was precisely weighed and placed in a 5 mL vial; and 1.0 µL of 10 vol % acetic acid/methylene chloride was added with a micro-syringe, to give preparation as acetic acid content being 3.8%.

Reference Example 5

(1) A 5.05 mg of dried mass obtained in Example 6(1) was precisely weighed and placed in a 5 mL vial; and 1.7 µL of 10 vol % acetic acid/methylene chloride was added with a micro-syringe, to give preparation as acetic acid content being 5.2%.

(2) A 5.59 mg of dried mass obtained in Example 6(1) was precisely weighed and placed in a 5 mL vial; and 2.5 µL of 10 vol % acetic acid/methylene chloride was added with a micro-syringe, to give preparation as acetic acid content being 6.4%.

(3) A 5.01 mg of dried mass obtained in Example 6(1) was precisely weighed and placed in a 5 mL vial; and 3.0 µL of 10 vol % acetic acid/methylene chloride was added with a micro-syringe, to give preparation as acetic acid content being 8.0%.

(4) A 5.48 mg of dried mass obtained in Example 6(1) was precisely weighed and placed in a 5 mL vial; and 4.4 µL of 10 vol % acetic acid/methylene chloride was added with a micro-syringe, to give preparation as acetic acid content being 10.2%.

(5) A 5.47 mg of dried mass obtained in Example 6(1) was precisely weighed and placed in a 5 mL vial; and 5.5 µL of 10 vol % acetic acid/methylene chloride was added with a micro-syringe, to give preparation as acetic acid content being 12.3%.

(6) A 5.10 mg of dried mass obtained in Example 6(1) was precisely weighed and placed in a 5 mL vial; and 10.2 µL of 10 vol % acetic acid/methylene chloride was added with a micro-syringe, to give preparation as acetic acid content being 22.9%.

(7) A 5.53 mg of dried mass obtained in Example 6(1) was precisely weighed and placed in a 5 mL vial; and 16.6 µL of 10 vol % acetic acid/methylene chloride was added with a micro-syringe, to give preparation as acetic acid content being 33.6%.

Experiment 1

Stability of hPTH(1-34) (1)

The hPTH preparation from which acetic acid existing as the constituent of a salt of hPTH or an adherent, had been removed was tested for its stability.

An amount of preparation corresponding to about 150 mg as hPTH(1-34) obtained as acetic acid content being 9.5% introduced into a glass vial and helmetically sealed as obtained in Reference Example 1 was stored in an LH-30-14 depository (Nagano Science Co.) kept at 40±1° C. for six months. Prior to storage, some vials and after storage the remaining vials were subjected to reverse phase HPLC, thereby isolating decomposition products (by-products) prior to storage as well as subsequent to storage for their structural analysis. The results are shown in Table 2.

The reverse phase HPLC chromatogram of the sample having undergone storage is shown in FIG. 1. A high peak representing hPTH(1-34) was followed by three peaks (retention time being 13 to 17 minutes) designated as B, C and D. The percent areas of those peaks are 3.9% for peak B, 6.9% for peak C, and 3.0% for peak D as indicated in Table 2. The total is 13.8% or a considerable fraction which forms a major cause for the deterioration of the product. Structural analysis was introduced to identify the compounds responsible for respective peaks and demonstrated peak B is represented by a mixture of [Nε-acetyl-Lys$^{13}$]-hPTH(1-34) and [Nε-acetyl-Lys$^{26}$]-hPTH(1-34), peak C by [Nα-acetyl-Ser$^{1}$]-hPTH(1-34), and peak D by [Nε-acetyl-Lys$^{27}$]-hPTH(1-34).

Next, the hPTH(1-34) preparation as acetic acid content being 2.9% as obtained in Example 1(3) was studied for its stability in the same manner as above.

An amount of preparation corresponding to about 150 mg as hPTH(1-34) obtained as acetic acid content being 2.9% introduced into a glass vial and helmetically sealed was stored in an LH-30-14 depository (Nagano Science Co.) kept at 40±1° C. for six months. Prior to storage, some vials and after storage the remaining vials were subjected to reverse phase HPLC, thereby isolating decomposition products (by-products) prior to storage as well as subsequent to storage for their structural analysis. The results are shown in Table 3.

Figure 2:
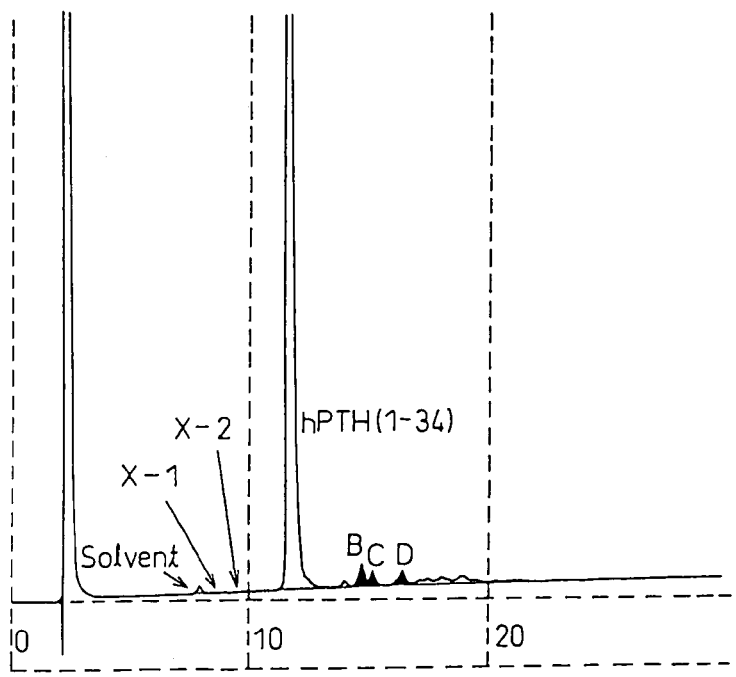
FIG. 2 shows a reverse phase HPLC chromatogram obtained from an hPTH(1-34) preparation as acetic acid content being 2.9% after it has been stored at 40° C. for six months.

The reverse phase HPLC chromatogram of the sample having undergone storage is shown in FIG. 2. As is obvious from FIG. 2, when it is compared with the one from the hPTH(1-34) as acetic acid content being 9.5%, all the areas of peaks B, C and D are reduced. The areas of peaks B, C and D are in total 0.2% which is similar to the corresponding value observed in the hPTH(1-34) as acetic acid content being 9.5%. The post-storage value of the total peak areas here concerned is 3.6%, which is far below the corresponding value (13.8%) of the hPTH(1-34) as acetic acid content being 9.5%.

It was demonstrated from above that acetyl bodies are major decomposition products derived from hPTH, and that reduction of the content of acetic acid existing as the constituent of a salt of hPTH(1-34) or an adherent will lead to an improved stability of the hPTH. Namely, reduction of the acetic acid content of an hPTH preparation will lead to the production of an hPTH-based pharmaceutical component having an excellent stability.

TABLE 2

Stability of hPTH(1–34) (acetic acid content: 9.5%, storage at 40° C. for 6 months)

| Peak | Decomposition products (by-products) | Before storage (peak area %) | After storage (peak area %) |
|---|---|---|---|
| X1 | [Met(O)$^8$]-hPTH(1–34) | 0.1% or less | 0.1% |
| X2 | [Met(O)$^{18}$]-hPTH(1–34) | 0.1% or less | 0.1% |
| B* | [Nε-AcLys$^{18}$]-hPTH(1–34) [Nε-AcLys$^{26}$]-hPTH(1–34) | Not detected | 3.9% |
| C | [Nα-AcSer$^1$]-hPTH(1–34) | 0.2% | 6.9% |
| D | [Nε-AcLys$^{27}$]-hPTH(1–34) | Not detected | 3.0% |
| Others | Unidentified decomposition products | 0.1% | 4.9% |
| hPTH(1–34) | | 99.6% | 81.1% |
| Total | | 100.0% | 100.0% |

*Peak B represents a mixture.

TABLE 3

Stability of hPTH(1–34) (acetic acid content: 2.9%, storage at 40° C. for 6 months)

| Peak | Decomposition products (by-products) | Before storage (peak area %) | After storage (peak area %) |
|---|---|---|---|
| X1 | [Met(O)$^8$]-hPTH(1–34) | 0.1% | 0.1% |
| X2 | [Met(O)$^{18}$]-hPTH(1–34) | 0.1% | 0.1% |
| B* | [Nε-AcLys$^{18}$]-hPTH(1–34) [Nε-AcLys$^{26}$]-hPTH(1–34) | Not detected | 1.4% |
| C | [Nα-AcSer$^1$]-hPTH(1–34) | 0.2% | 1.0% |
| D | [Nε-AcLys$^{27}$]-hPTH(1–34) | Not detected | 1.2% |
| Others | Unidentified decomposition products | 0.1% | 3.9% |
| hPTH(1–34) | | 99.5% | 92.3% |
| Total | | 100.0% | 100.0% |

*Peak B represents a mixture.

Experiment 2

Stability of hPTH(1-34) (2)

Stored at 80° C. for 15 hours were hPTH(1-34) preparations as obtained in Example 4 and Reference Example 4 which contained the respective contents of acetic acid contents as specified in Example 4 and Reference Example 4; to each of the preparations was added 15 mL of distilled water with a syringe; and for each preparation, its content of decomposition products (by-products) was determined before and after storage. The results are shown in Table 4. The content (%) of acetyl bodies (B, C and D) of each hPTH(1-34) preparation after storage is plotted as a function of its acetic acid content in FIG. 3.

Figure 3:
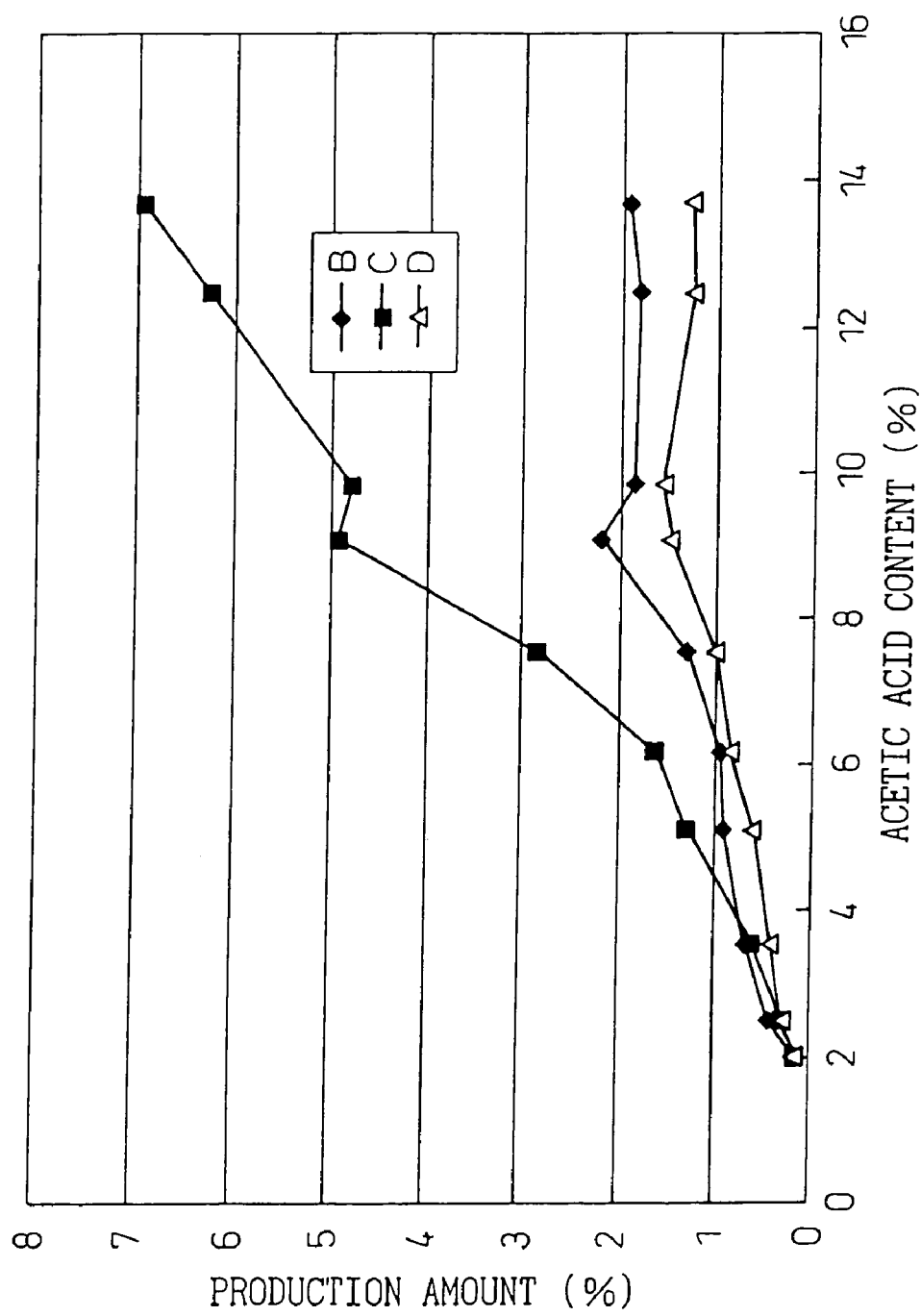
FIG. 3 shows the amounts of decomposition products (by-products) B, C and D after hPTH(1-34) preparations contained various acetic contents acid have been stored at 80° C. for 15 hours.

As is obvious from Table 4 and FIG. 3, with the reduction of acetic acid content, decomposition products B, C and D derived from acetyl bodies decrease.

Figure 4:
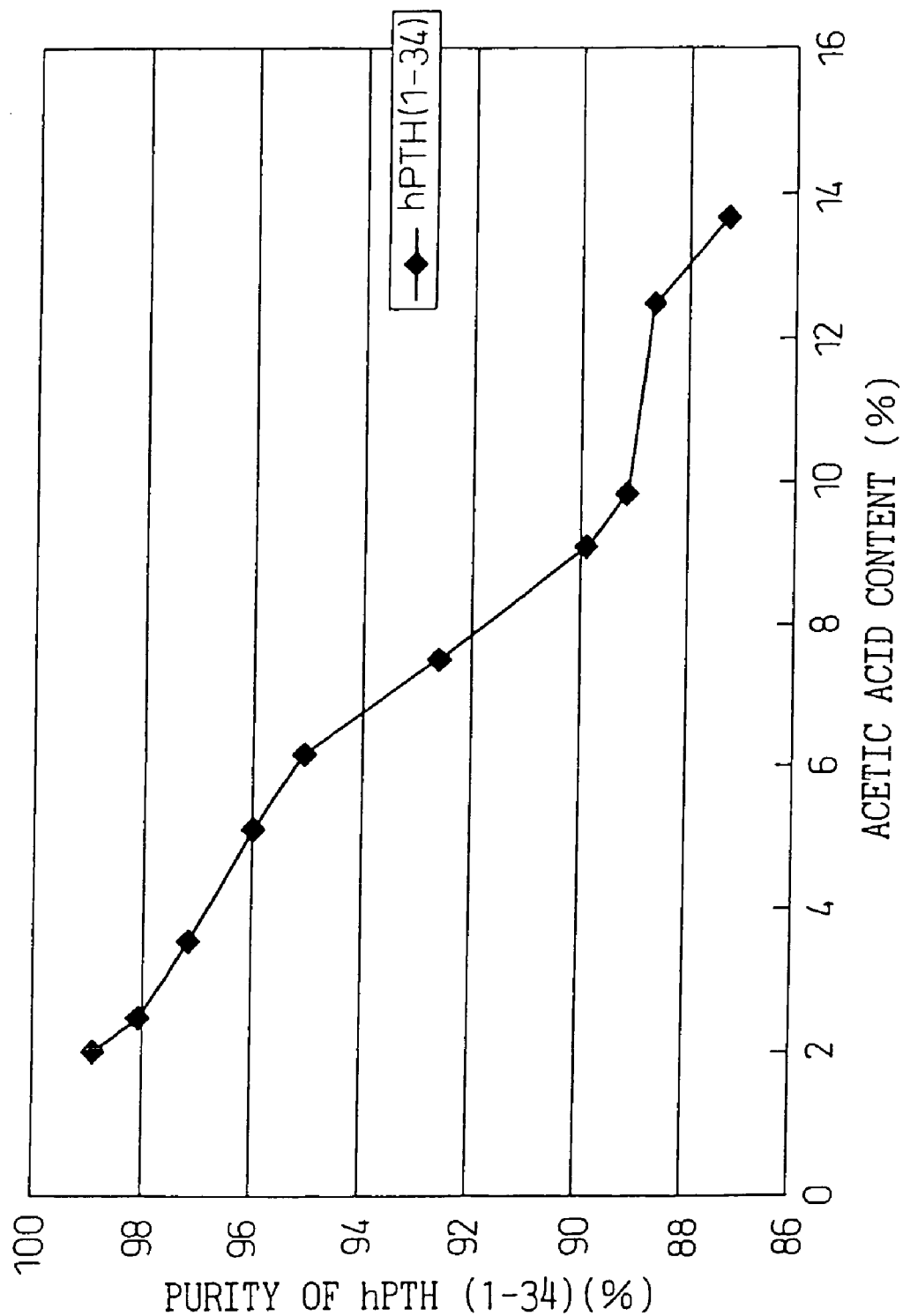
FIG. 4 shows the purity levels of hPTH(1-34) of the hPTH(1-34) preparations contained various acetic acid content after the preparations have been stored at 80° C. for 15 hours.

The purity of hPTH(1-34) preparations was plotted as a function of their acetic acid contents in FIG. 4. As is obvious from FIG. 4, the curve takes a sigmoid course with a deflection point at the chemical equivalent (acetic acid content equal to about 7.3%) and if the acetic acid content is kept below the chemical equivalent, the stability of the product is rapidly improved.

Namely, reduction of the acetic acid content of an hPTH preparation will lead to the production of an hPTH-based pharmaceutical component having an excellent stability.

TABLE 4

Stability of hPTH(1–34) (storage at 80° C. for 15 hours)

| Decomposition products | Acetic acid content (%) | | | | | | | | | | | |
|---|---|---|---|---|---|---|---|---|---|---|---|---|
| | 2.0 | 2.5 | 3.6 | 5.1 | 6.2 | 7.5 | 9.1 | 9.9 | 12.5 | 13.7 | 18.3* | 72.5* |
| X1 (%) | ND | ND | ND | ND | ND | ND | ND | ND | ND | ND | ND | ND |
| X2 (%) | ND | ND | ND | ND | ND | ND | ND | ND | ND | ND | ND | ND |
| B (%) | 0.15 | 0.43 | 0.64 | 0.91 | 0.95 | 1.32 | 2.19 | 1.87 | 1.82 | 1.93 | 2.75 | 5.24 |
| C (%) | 0.09 | 0.28 | 0.61 | 1.30 | 1.63 | 2.85 | 4.92 | 4.80 | 6.25 | 6.92 | 17.8 | 19.5 |
| D (%) | 0.16 | 0.27 | 0.40 | 0.60 | 0.87 | 1.04 | 1.50 | 1.58 | 1.28 | 1.31 | 1.82 | 2.8 |
| Others (%) | 0.74 | 0.93 | 1.10 | 1.14 | 1.48 | 2.22 | 1.45 | 2.54 | 1.91 | 2.58 | 12.4 | 39.9 |

TABLE 4-continued

Stability of hPTH(1–34) (storage at 80° C. for 15 hours)

| Decomposition products | Acetic acid content (%) | | | | | | | | | | | |
|---|---|---|---|---|---|---|---|---|---|---|---|---|
| | 2.0 | 2.5 | 3.6 | 5.1 | 6.2 | 7.5 | 9.1 | 9.9 | 12.5 | 13.7 | 18.3* | 72.5* |
| hPTH(1–34) (%) | 98.9 | 98.1 | 97.2 | 96.0 | 95.1 | 92.6 | 89.9 | 89.2 | 88.7 | 87.3 | 65.2 | 32.6 |

ND: Not detected
*Occurs as a liquid after storage.
X1: [Met(O)$^8$]-hPTH(1–34)
X2: [Met(O)$^{18}$]-hPTH(1–34)
B: Mixture of [Nε-AcLys$^{18}$]-hPTH(1–34) and [Nε-AcLys$^{26}$]-hPTH (1–34)
C: [Nα-AcSer$^1$]-hPTH(1–34)
D: [Nε-AcLys$^{27}$]-hPTH(1–34)

Experiment 3

Stability of hPTH(1-84)

Figure 5:
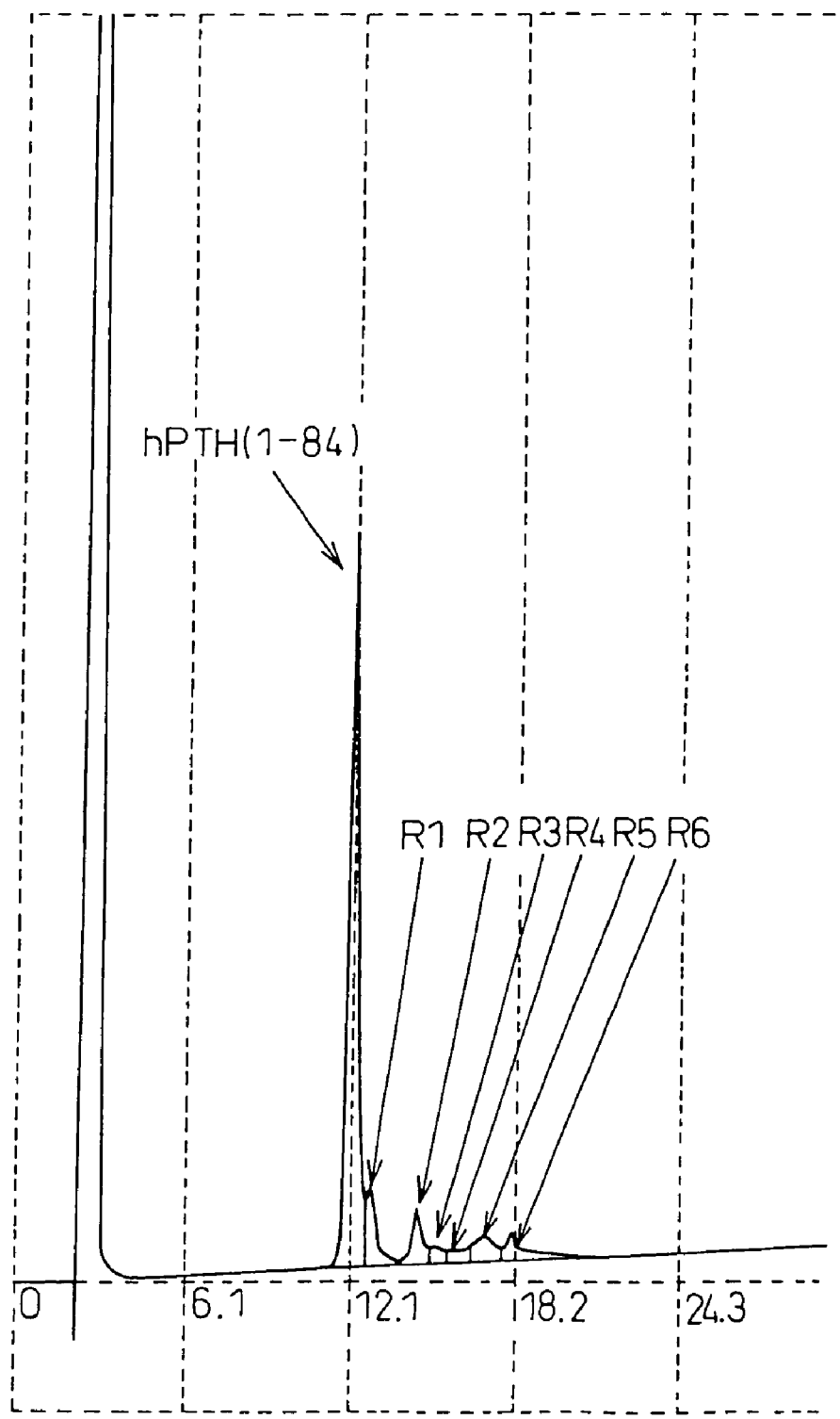
FIG. 5 shows a reverse phase HPLC chromatogram of an hPTH(1-84) preparation as acetic acid content being 12.3% after it has been stored at 80° C. for 15 hours.
Figure 6:
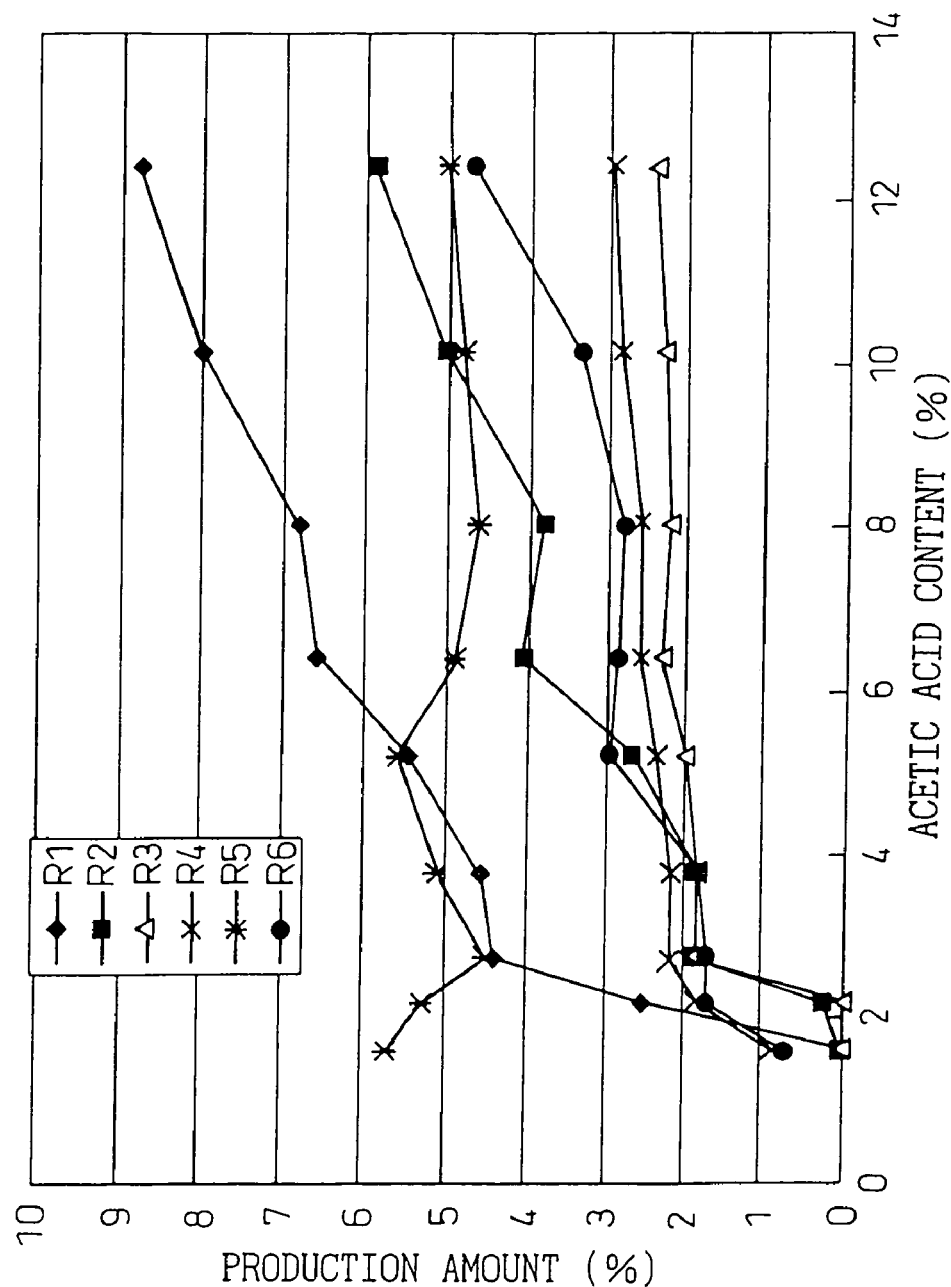
FIG. 6 shows the amounts of decomposition products (by-products) after hPTH(1-84) preparations contained various acetic acid contents have been stored at 80° C. for 15 hours.

Stored at 80° C. for 15 hours were hPTH(1-84) preparations as obtained in Example 6 and Reference Example 5 which contained the respective acetic acid contents as specified in Example 6 and Reference Example 5; and each of the preparations was left to stand at room temperature for one minute to allow methylene chloride to vaporize, and then capped. Those hPTH(1-84) preparations contained the respective acetic acid contents were stored at 80° C. for 15 hours; 1 mL of distilled water was added to each of the preparations with a syringe for dissolution; and for each preparation, its content of decomposition products (by-products) was determined before and after storage. The results are shown in Table 5. The reverse phase HPLC chromatogram of the sample having undergone storage is shown in FIG. 5. In addition, the contents (%) of decomposition products (by-products) of each hPTH(1-84) preparation after storage is plotted as a function of its acetic acid content in FIG. 6.

As shown in FIG. 5, decomposition products (by-products) designated as R1 to R6 were produced as a result of storage. It was demonstrated from Table 5 and FIG. 6 that decomposition products other than the one designated as R5 increase as a function of acetic acid content.

The post-storage purity of hPTH(1-84) preparations was plotted as a function of their acetic acid contents in FIG. 7. The purity of hPTH(1-84) preparation increases with the reduction of its acetic acid content, and rises sharply when the acetic acid content falls below the chemical equivalent (about 4.5%). From above results it was suggested although the hPTH(1-84) preparation contains certain decomposition products whose content is independent of the content of coexistent acetic acid, for the development of the majority of decomposition products is closely involved acetic acid that exists as the constituent of a salt of hPTH(1-84) or as an adherent, as in hPTH(1-34). Namely, reduction of the acetic acid content of an hPTH preparation will lead to the production of an hPTH-based pharmaceutical component having an excellent stability.

TABLE 5

Stability of hPTH(1–84) (storage at 80° C. for 15 hours)

| Decomposition products | Acetic acid content (%) | | | | | | | | | | |
|---|---|---|---|---|---|---|---|---|---|---|---|
| | 1.6 | 2.2 | 2.7 | 3.8 | 5.2 | 6.4 | 8.0 | 10.2 | 12.3 | 22.9 | 33.6 |
| R1 (%) | ND | 2.52 | 4.38 | 4.55 | 5.46 | 6.60 | 6.82 | 8.04 | 8.8 | 12.0 | 12.4 |
| R2 (%) | 0.05 | 0.24 | 1.83 | 1.85 | 2.67 | 4.05 | 3.80 | 5.03 | 5.91 | 11.3 | 14.8 |
| R3 (%) | ND | ND | 1.82 | 1.80 | 2.00 | 2.31 | 2.22 | 2.28 | 2.45 | 3.21 | 9.32 |
| R4 (%) | 0.88 | 1.83 | 2.18 | 2.15 | 2.39 | 2.57 | 2.59 | 2.86 | 2.96 | 3.41 | 6.61 |
| R5 (%) | 5.68 | 5.27 | 4.48 | 5.11 | 5.56 | 4.89 | 4.62 | 4.82 | 5.03 | 5.89 | 5.13 |
| R6 (%) | 0.68 | 1.66 | 1.66 | 1.83 | 2.94 | 2.83 | 2.76 | 3.33 | 4.70 | 6.87 | 12.2 |
| hPTH(1–84) (%) | 92.8 | 88.5 | 83.6 | 82.7 | 79.0 | 76.7 | 77.2 | 73.6 | 70.1 | 57.3 | 39.6 |

ND: Not detected

Experiment 4

Sensory Test (1)

For the hPTH-based medicinal component, assessment of its use feeling was achieved by applying it into the nasal cavity.

The hPTH(1-34) preparation prepared as in Reference Example 1 was dissolved in 0.6 w/v % aqueous solution of citric acid or in water to 10 mg/mL; the solution was transferred in a screw type glass vial; a spray nozzle (50 μL) (Valois Co.) was attached to the viol; 50 μL of the solution was sprayed into one nasal cavity; and the odor and irritation evoked by nasal spraying were assessed (testers consisting of 12 healthy normal adult males). The odor was ranked in four stages as "acidic odor present," "acidic odor slightly present," "a slight odor detected," and "no odor detected" according to the olfactory sensation in the tester. The irritation was ranked in four stages as "painfully irritating," "strongly irritating," "weakly irritating," and "very weakly irritating." Then, the odor and irritation were scored according to their rank. As the control, physiological saline was used. The results are shown in Table 6.

As is obvious from Table 6, the hPTH(1-34) preparation dissolved in aqueous solution of citric acid and the aqueous solution of hPTH(1-34) preparation evoked a strong acidic odor to cause a discomfort in the tester.

Then, aqueous solutions of various organic acids were prepared, in order to identify the factors responsible for the odor and irritation the preparation evokes when it is applied in the nasal cavity. The organic acid employed included acetic acid, citric acid and tartaric acid; oxalic acid; malic acid; phthalic acid; ascorbic acid; adipic acid; and glycolic acid.

Prepared were 0.1 v/v %, 0.2 v/v %, 0.3 v/v % and 0.6 v/v % aqueous solutions of acetic acid, and 0.6 w/v % aqueous solutions of citric acid, tartaric acid, oxalic acid, malic acid, phthalic acid, ascorbic acid, adipic acid, and glycolic acid. The solution was sprayed into the nasal cavity; and the odor and irritation were assessed in the same manner as above (testers consisting of four healthy normal adult males). The results are shown in Table 6. As is obvious from Table 6, 0.3 v/v % or higher concentrated aqueous solutions of acetic acid evoke a strong acidic odor, and the irritating activity therefrom also rapidly increases when the acetic acid concentration becomes 0.3 v/v % or higher.

On the other hand, the aqueous solutions of other organic acids do not evoke any detectable odor, and the irritation evoked in the nasal cavity by the aqueous solution of citric acid, together with those of ascorbic acid, adipic acid and glycolic acid, is the same with that from physiological saline.

The hPTH(1-34) preparation as acetic acid content being 9.5% obtained in Reference Example 1, and the amount of acetic acid contained in this preparation was approximately the same with the corresponding values of the hPTH(1-34) solution and of 0.1 v/v % aqueous solution of acetic acid used in this test.

From the above results, it is suggested that, since 0.6 w/v % aqueous solution of citric acid itself does not evoke any detectable odor, the odor evoked by the hPTH preparation dissolved in 0.6 w/v % aqueous solution of citric acid could be ascribed to acetic acid existing as the constituent of a salt of hPTH(1-34) or as an adherent to the salt in the preparation, even though acetic acid as contained in the hPTH preparation would not evoke any detectable odor, if it exists as an aqueous solution, that is, in combination with water.

The hPTH(1-34) preparation as acetic acid content being 2.9% prepared as in Example 1(3) was dissolved in 0.4 w/v % aqueous solution of citric acid to 5 mg/mL. In the same manner as above, the test solution was applied in the nasal cavity, and the odor and irritation evoked thereby were assessed (testers consisting of 12 healthy normal adult males). The results are shown in Table 6. As is obvious from Table 6, it is indicated that reducing the content of acetic acid in the preparation will inhibit the odor and irritability of the preparation, and thus the preparation which has a reduced content of acetic acid will become a pharmaceutical component which will ensure an excellent use feeling when incorporated into a pharmaceutical composition for practical use.

TABLE 6

Irritability and odor of aqueous solutions of hPTH(1–34) and of various organic acids

| hPTH/organic acid | Irritability | Odor |
| --- | --- | --- |
| hPTH(1–34)*[1] | ++ | Acidic odor present |
| hPTH(1–34)*[2] | + | Acidic odor present |
| Physiological saline | + | No odor present |
| Acetic acid (0.6 v/v % aqueous solution) | +++ | Acidic odor present |
| Acetic acid (0.3 v/v % aqueous solution) | +++ | Acidic odor present |
| Acetic acid (0.2 v/v % aqueous solution) | + | Slight acidic odor present |
| Acetic acid (0.1 v/v % aqueous solution) | + | Scarcely any odor present |
| Citric acid (0.6 w/v % aqueous solution) | + | No odor present |
| Tartaric acid (0.6 w/v % aqueous solution) | ++++ | No odor present |
| Oxalic acid (0.6 w/v % aqueous solution) | ++++ | No odor present |
| Malic acid (0.6 w/v % aqueous solution) | ++++ | No odor present |
| Phthalic acid (0.6 w/v % aqueous solution) | +++ | No odor present |
| Ascorbic acid (0.6 w/v % aqueous solution) | + | No odor present |
| Adipic acid (0.6 w/v % aqueous solution) | + | No odor present |
| Glycolic acid (0.6 w/v % aqueous solution) | + | No odor present |
| hPTH(1–34)*[3] | + | Slight acidic odor present |

++++: Painfully irritation,
+++: Strong irritation
++: Weak irritation
+: Very weak irritation
*[1] 10 mg/mL hPTH(1–34) solution (acetic acid content being 9.5%) dissolved in 0.6 w/v % aqueous solution of citric acid
*[2] 10 mg/mL aqueous solution of hPTH(1–34) (acetic acid content being 9.5%)
*[3] 5 mg/mL hPTH(1–34) solution (acetic acid content being 2.9%) dissolved in 0.4 w/v % aqueous solution of citric acid Experiment 5

Sensory Test (2)

(1) Preparation of Test Solutions

An amount of preparation corresponding to 300 mg as hPTH(1-34) obtained as acetic acid content being about 9.5% in Reference Example 1 was dissolved in distilled water (30 mL), to give an aqueous solution of hPTH(1-34) at 10 mg/mL. The solution (pH4.7) was subjected to electrodialysis for removal of acetic acid using a micro acilyser (Asahi Kasei Corp.) incorporating an electrodialysis membrane AC-130-10 (Asahi Kasei Corp.) until the dialysis solution had a pH of 5.0 (acetic acid content being 7.3%). An aqueous solution of hPTH(1-34) considerably removed of acetic acid was obtained.

Some aqueous solution of hPTH(1-34) was similarly subjected to electrodialysis until pH6.0 was reached (acetic acid content being 2.9%), to give an aqueous solution of hPTH(1-34) considerably removed of acetic acid. A same aqueous solution of hPTH(1-34) was similarly treated until pH 7.6 was reached (acetic acid content being 0.5%), to give an aqueous solution of hPTH(1-34) largely removed of acetic acid.

(2) Sensory Test

To 1.5 mL of each test solution prepared in this testing example (1), was added 1.5 mL of aqueous solution containing 270 mg of purified sucrose, 12 mg of citric acid, and 0.3 mg of benzalkonium chloride, and the mixture was employed as a test solution for intranasal application. The solution was transferred in a screw type glass vial with a stopper; and a spray nozzle (50 µL)(Valois) was attached to the vial for the test (testers consisting of 5 healthy normal adult males). The odor was classified as "A: scarcely any acetic acid odor detected," "B: weak acetic acid odor detected," and "C: strong acetic acid odor detected." The irritation was classified as "A: no irritation felt," "B: more or less irritation felt," and "C: strong irritation felt." Then, the odor and irritation were scored according to their classification. The results are shown in Table 7.

As is obvious from Table 7, it is indicated that reducing the content of acetic acid in the preparation will inhibit the odor and irritability of the preparation, and thus the preparation which has a reduced content of acetic acid will become a pharmaceutical component which will ensure an excellent use feeling to be suitable for a protracted use when incorporated into a pharmaceutical composition for practical use.

TABLE 7

Sensory test of hPTH(1–34)-based pharmaceutical products containing various amounts of acetic acid

| Subject | Acetic acid content 9.5% | | Acetic acid content 7.3% | | Acetic acid content 2.9% | | Acetic acid content 0.5% | |
|---|---|---|---|---|---|---|---|---|
| | Odor | Irritability | Odor | Irritability | Odor | Irritability | Odor | Irritability |
| ① | B | B | B | B | B | B | A | A |
| ② | B | B | A | B | A | B | A | B |
| ③ | C | B | B | A | A | A | A | A |
| ④ | C | B | B | A | A | A | A | A |
| ⑤ | A | B | B | A | B | A | A | A |

Odor
A: Scarcely any acidic odor detected
B: Weak acidic odor detected
C: Strong acidic odor detected
Irritability
A: No irritation felt
B: More or less irritation felt
C: Strong irritation felt Experiment 6

Effects of Various Organic Acids on the Stability of hPTH Preparations

Removal of acetic acid content from an hPTH preparation may be achieved by electrodialysis as mentioned earlier, but it may be achieved by replacing the acetic acid with another organic acid.

If the acetic acid component of an hPTH preparation is replaced with another organic acid, how the newly introduced organic acid will affect the stability of the hPTH preparation was assessed.

The organic acid used in this test included adipic acid, citric acid and glycolic acid which are known as absorption stimulants, and had been found in Testing Example 4 as giving a good use feeling. The organic acid the addition of which was intended to replace acetic acid bound with hPTH was added at a concentration equal to the chemical equivalent of acetic acid. An hPTH(1-34) molecule contains nine basic amino acid residues and four acidic amino acid residues, that is, an hPTH(1-34) molecule has five positive charges available for binding with acid to form a salt therewith. Thus, with one mol of hPTH(1-34) (Mw. 4117.8) will bind 5/2 mol of adipic acid (Mw. 146.14), 5/3 mol of citric acid (Mw. 192.13), or 5 mol of gylicolic acid (Mw. 76.05), to form a salt. Adipic acid, citric acid or glycolic acid was added to the test hPTH preparation, so as to satisfy the respective mol proportion described above.

A hPTH(1-34) preparation as acetic acid content being 2.9% obtained in Example 1(3) was used to prepare an aqueous solution of hPTH(1-34) at 5 mg/mL.

To 2 mL of this solution (10 mg of hPTH(1-34) or 2.43 µmol), was added 888 µg of adipic acid (2.43×5/2 µmol), 778 µg of citric acid (2.43×5/3 µmol), or 924 µg of glycolic acid (2.43×5 µmol). Each solution was adjusted with distilled water such that the resulting solution contained the peptide at 1 mg/mL. The solution was lyophilized, to give a lyophilized sample containing 10 mg of hPTH(1-34). For samples thus prepared, some were subjected to reverse phase HPLC to give a pre-storage purity of hPTH; others were stored at 60° C. for three weeks; then they were similarly subjected to reverse phase HPLC, to give a post-storage purity of hPTH; and the pre- and post-storage purity values were compared to assess the stability of the hPTH preparation. An hPTH(1-34) preparation as acetic acid content being 2.9% prepared in Example 1(3) was used as control. The results are shown in Table 8.

While the post-storage purity of the hPTH preparation as acetic acid content being 2.9% was 92.7%, the same preparation, when receiving the addition of adipic acid, citric acid or glycolic acid before storage, showed post-storage purity values of 92.0, 93.9 and 90.3%, respectively. It is indicated from this that an hPTH pharmaceutical component supplemented with adipic acid, citric acid or glycolic acid will be highly stable, and ensure a good use feeling like an hPTH pharmaceutical component in which the content of acetic acid existing as the constituent of a salt of hPTH or an adherent has been reduced.

It is also indicated that a pharmaceutical component can be obtained by replacing acetic acid existing in an hPTH preparation as the constituent of a salt or an adherent with a certain organic acid, will serve as a pharmaceutical component similarly to an hPTH preparation whose acetic acid content has been reduced. It is further indicated that the component, which is highly stable and will ensure an excellent use feeling if incorporated into a pharmaceutical composition, has also a feature of compatibly receiving the addition of an organic acid which may be added to improve the absorption of the component.

TABLE 8

Effects of various organic acids on the stability of hPTH (storage at 60° C./3 weeks)

| | Acetic acid | | Adipic acid | Citric acid | Glycolic acid |
|---|---|---|---|---|---|
| hPTH(1–34) | 9.5% | 2.9% | 8.8% | 7.7% | 9.2% |

TABLE 8-continued

Effects of various organic acids on
the stability of hPTH (storage at 60° C./3 weeks)

|  | Acetic acid | Adipic acid | Citric acid | Glycolic acid |
|---|---|---|---|---|
| Acid content* Purity before storage (%) | 99.8% | 99.8% | 100.0% | 100.0% | 100.0% |
| Purity after storage (%) | 73.2% | 92.7% | 92.0% | 93.9% | 90.3% |

*Acid content = acid weight × 100(%)/peptide weight of hPTH

Experiment 7

Test of Absorption through Nasal Mucosa

When designing a pharmaceutical composition for intranasal administration from the preparation, the absorption of the preparation through the nasal mucosa becomes an important factor. In view of this, the absorption of the preparation through the nasal mucosa was tested. The effects of citric acid and ascorbic acid which were found in Testing Example 4 to give a good use feeling when added to the hPTH preparation, on the nasal absorption of hPTH were assessed by following the areas under curve (AUC) of an hPTH plasma concentration-time curve, and the bioavailability of hPTH.

hPTH(1-34) preparation as acetic acid content being 2.9% prepared in Example 1(3) were dissolved in 0.3 and 0.6 w/v % aqueous solutions of ascorbic acid, and in 0.2, 0.3, 0.4 and 0.6 w/v % aqueous solutions of citric acid, to give hPTH solutions at 5 mg/mL. Similarly, an hPTH(1-34) preparation as acetic acid content being 0.9% prepared in Example 5(4) was dissolved in 0.6 w/v % aqueous solution of citric acid, to give a peptide solution at 10 mg/mL. As control were used an hPTH(1-34) preparation as acetic acid content being 2.9% prepared in Example 1(3) and an hPTH(1-34) preparation as acetic acid content being 0.9% prepared in Example 5(4), both being dissolved in physiological saline.

Further, hPTH(1-34) preparations as acetic acid content being 2.9% prepared in Example 1(3) were dissolved in 0.3 w/v % or 0.6 w/v % aqueous solution of citric acid; to this solution was added camostat mesilate known as an inhibitor of proteinase to 0.3 w/v %; and the resulting solution was used for the test.

Seven to nine week old Sprague-Dawley male rats (Crj: CD, Charles River Japan, Inc.) were kept in metal cages at 22±5° C. and 30–70% relative humidity with a dark-light cycle changing at 12 hour intervals, being allowed to freely fed on food pellets and tap water. For twenty-four hours prior to test, they had been fasted (a group consisting of five rats).

For intranasal administration, the rat, while being kept under pentobarbital anesthesia, had a cannule inserted through a femoral artery; and 5 µL of test solution, or 10 µL of benzalkonium chloride containing sucrose was administered into the nasal cavity with a Pipetman (TM). Blood was sampled through the cannule into a tube containing an anticoagulant and proteinase inhibitor; and the blood was centrifuged to give plasma. The concentrations of hPTH(1-34) and hPTH(1-84) in plasma were determined by RIA using anti PTH(1-34) antibodies (Chemicon International Inc.)

For subcutaneous administration, the rat received on its back the subcutaneous injection of the test solution at 1 mL/kg, and the concentration of hPTH in plasma was determined in the same manner as in nasal administration.

The bioavailabilities of hPTH(1-34) and hPTH(1-84) were obtained by calculation from the ratios of the plasma concentrations three (hPTH(1-34)) or six (hPTH(1-84)) hours after subcutaneous administration respectively against the corresponding AUCs of a plasma concentration-time curve. The results are shown in Table 9.

Although the bioavailability of hPTH(1-34) subcutaneously applied was 1.4% when hPTH(1-34) was used alone, it increased to 5 to 10%, or 12 to 19% when it was used as a solute of 0.3 to 0.6 w/v % ascorbic acid, or of 0.2 to 0.6 w/v % citric acid.

The bioavailability of hPTH(1-84) was about 30% when it was used as a solute of 0.6 w/v % aqueous solution of citric acid.

Further, when hPTH(1-34) was applied being dissolved in a solution supplemented with camostat mesilate or a proteinase inhibitor, its bioavailability was 27 to 31%.

From this it was indicated that addition of the organic acids to a small concentration notably improves the absorption of hPTH preparations through the nasal mucosa. It was also recognized addition of the absorption stimulator further improves the nasal absorption of hPTH preparations. In conclusion, it was demonstrated an hPTH-based pharmaceutical composition incorporating an hPTH-based pharmaceutical component intended for intranasal use is suitably used as such because the pharmaceutical component is highly stable, and ensures an excellent use feeling when administered intra-nasally, as the acetic acid content thereof existing as the constituent of a salt or as an adherent being deliberately reduced.

TABLE 9

Nasal absorption of hPTH(1–34) and hPTH(1–84) (rat)

| Prescription | Dose | Route | AUC (pg × hr/mL) | Bioavailability (% s.c.) |
|---|---|---|---|---|
| hPTH(1–34) (Saline) | 25 µg/kg | Subcutaneous | 1356.5 ± 503.4 | (100) |
| hPTH(1–34) (Saline) | 125 µg/kg | Intra-nasal | 93.7 ± 61.3 | 1.4 |
| 0.3 w/v % Ascorbic acid | 125 µg/kg | Intra-nasal | 357.4 ± 308.3 | 5.2 |
| 0.6 w/v % Ascorbic acid | 125 µg/kg | Intra-nasal | 687.3 ± 281.9 | 9.9 |

TABLE 9-continued

Nasal absorption of hPTH(1–34) and hPTH(1–84) (rat)

| Prescription | Dose | Route | AUC (pg × hr/mL) | Bioavailability (% s.c.) |
|---|---|---|---|---|
| 0.2 w/v % Citric acid | 125 μg/kg | Intra-nasal | 838.4 ± 407.9 | 12.2 |
| 0.3 w/v % Citric acid | 125 μg/kg | Intra-nasal | 1208.9 ± 618.6 | 17.6 |
| 0.4 w/v % Citric acid | 125 μg/kg | Intra-nasal | 1285.2 ± 572.4 | 18.7 |
| 0.6 w/v % Citric acid | 125 μg/kg | Intra-nasal | 1254.9 ± 526.1 | 18.3 |
| 0.3 w/v % Citric acid + 0.3 w/v % Camostat | 125 μg/kg | Intra-nasal | 2118.0 ± 860.4 | 30.8 |
| 0.6 w/v % Citric acid + 0.3 w/v % Camostat | 125 μg/kg | Intra-nasal | 1829.4 ± 1072.7 | 27.0 |
| hPTH(1–84) (Saline) | 285 μg/kg | Subcutaneous | 46833.3 ± 15667 | (100) |
| hPTH(1–84) 0.6 w/v % Citric acid | 285 μg/kg | Intra-nasal | 14166.7 ± 6833 | 30.2 |

Formulation Example 1

40.5 g of purified sucrose (Japanese Pharmacopoeia) was dissolved in 124.2 g of purified water (Japanese Pharmacopoeia) to prepare 150 mL of a 27 w/v % aqueous solution of purified sucrose. On the other hand, an amount of preparation corresponding to 1.5 g as hPTH(1-34) obtained as acetic acid content being 2.1% (ten vials) which was obtained in Example 2, was dissolved in about 75 mL of purified water (Japanese Pharmacopoeia) as a pharmaceutical component. A concentration of hPTH (1-34) in the solution was determined as 20.4 mg/mL by reverse phase HPLC. 25.9 mL of purified water was added to 72.0 mL of the solution to adjust the concentration to 15 mg/mL. 97 mL of 15 mg/mL hPTH (1-34) solution thus prepared, was taken and was mixed with 48.5 mL of the 27 w/v % purified sucrose aqueous solution which was prepared previously to obtain about 145 mL of hPTH (1-34) aqueous solution having a purified sucrose concentration of 9 w/v % and a hPTH (1-34) concentration of 10 mg/mL. 3mL of the solution was charged into each of 47 vials, and was freeze-dried in a freeze-drier, Model FZ-6 (Labconco Corporation), to obtain a stable pharmaceutical composition containing 270mg of purified sucrose and 30 mg of hPTH (1-34), per vial.

Formulation Example 2

40.5 g of purified sucrose (Japanese Pharmacopoeia) was dissolved in 124.2 g of purified water (Japanese Pharmacopoeia) to prepare 150 mL of a 27 w/v % aqueous solution of purified sucrose. On the other hand, as pharmaceutical component, an amount of preparation corresponding to 750 mg as hPTH(1-34) obtained as acetic acid content being 2.1% (five vials) which was obtained in Example 2, was dissolved in 146 mL of purified water (Japanese Pharmacopoeia) to obtain an aqueous solution of hPTH (1-34) having a hPTH (1-34) concentration of 5.1 mg/mL. Further, 54 mL of purified water (Japanese Pharmacopoeia) was added to the aqueous solution and agitated thoroughly to adjust the hPTH (1-34) concentration to 3.8 mg/mL (200 mL). 200 mL of the obtained solution with a hPTH (1-34) concentration of 3.8mg/mL was mixed with 100 mL of the 27 w/v % purified sucrose aqueous solution which was prepared previously, to obtain about 300 mL of a hPTH (1-34) aqueous solution having a purified sucrose concentration of 9 w/v % and a hPTH (1-34) concentration of 2.5mg/mL. 3mL of the solution was charged into each of 90 vials, and was freeze-dried in a freeze-drier, Model FZ-6 (Labconco Corporation), to obtain a stable pharmaceutical composition containing 270 mg of purified sucrose and 7.5 mg of hPTH (1-34), per vial.

Formulation Example 3

22.5 g of mannitol (Japanese Pharmacopoeia) was dissolved in 124.2 g of purified water (Japanese Pharmacopoeia) to prepare 150 mL of a 15% aqueous solution of mannitol. On the other hand, an amount of preparation corresponding to 1.5 g as hPTH(1-34) obtained as acetic acid content being 2.1% (ten vials), which was obtained in Example 2, was dissolved in about 75 mL of purified water (Japanese Pharmacopoeia) as a pharmaceutical component. A concentration of hPTH (1-34) in the solution was determined as 20.4 mg/mL by reverse phase HPLC. 25.9 mL of purified water was added to 72.0 mL of the solution to adjust the concentration to 15 mg/mL. 97 mL of 15 mg/mL hPTH (1-34) solution thus prepared, was taken and was mixed with 48.5 mL of the 15% mannitol aqueous solution which was prepared previously to obtain about 145 mL of hPTH (1-34) aqueous solution having a mannitol concentration of 5% and a hPTH (1-34) concentration of 10 mg/mL. 3mL of the solution was charged into each of 47 vials, and was freeze-dried in a freeze-drier, Model FZ-6 (Labconco Corporation), to obtain a stable pharmaceutical composition containing 150 mg of mannitol and 30 mg of hPTH (1-34), per vial.

Formulation Example 4

As a pharmaceutical component, 805 mg (powder weight) of a lyophilized product of hPTH (1-34) preparation as acetic acid content being 2.1%, which was obtained in Example 2, was weighed out and was dissolved in 360 mL of purified water (Japanese Pharmacopoeia) to obtain an aqueous solution with a hPTH (1-34) concentration of 2 mg/mL as determined by reverse phase HPLC. On the other hand, 1g of mannitol (Japanese Pharmacopoeia) was weighed out and was dissolved in 50 mL of purified water (Japanese Pharmacopoeia) to prepare a mannitol aqueous solution.

The whole of 50 mL of the mannitol aqueous solution and 50 mL of the hPTH (1-34) aqueous solution (2 mg/mL), which was prepared previously, were mixed well. 1 mL of the solution was dispensed into each of vials and was freeze-dried in a freeze-drier, Model FZ-6 (Labconco Corporation), to obtain a stable medicinal composition containing 1 mg of hPTH (1-34) and 10 mg of mannitol, per vial.

Formulation Example 5

As a pharmaceutical component, 805 mg (powder weight) of a lyophilized product of hPTH (1-34) preparation as acetic acid content being 2.1%, which was obtained in Example 2, was weighed out and was dissolved in 360 mL of purified water (Japanese Pharmacopoeia) to obtain an aqueous solution with a hPTH (1-34) concentration of 2 mg/mL as determined by reverse phase HPLC. On the other hand, 5 g of mannitol (Japanese Pharmacopoeia) was weighed out and was dissolved in 50 mL of purified water (Japanese Pharmacopoeia) to prepare a mannitol aqueous solution.

The whole of 50 mL of the mannitol aqueous solution and 50 mL of the hPTH (1-34) aqueous solution (2 mg/mL), which was prepared previously, were mixed well. 1 mL of the solution was dispensed into each of vials and was freeze-dried in a freeze-drier, Model FZ-6 (Labconco Corporation), to obtain a stable pharmaceutical composition containing 1 mg of hPTH (1-34) and 50 mg of mannitol, per vial.

Formulation Example 6

As a pharmaceutical component, about 11 mg (powder weight) of a lyophilized product of hPTH (1-34) preparation as acetic acid content being 2.1%, which was obtained in Example 2, was weighed out, and water for injection (WFI) (Japanese Pharmacopoeia) was added thereto to adjust the volume to 500 mL to obtain an hPTH (1-34) aqueous solution of 20 μg/mL as determined by reverse phase HPLC (solution A). 5 g of purified sucrose (Japanese Pharmacopoeia) and 100 mg of benzethonium chloride were dissolved in WFI (Japanese Pharmacopoeia) and a volume was adjusted to 100 mL (solution B). 30 mL each of the solutions A and B were mixed. The resulting solution was dispensed into each of vials by 1 mL per vial, and freeze-dried in a freeze-drier, Model FZ-6 (Labconco Corporation), to obtain a stable pharmaceutical composition containing 10 μg of hPTH (1-34), 25 mg of purified sucrose and 0.5 mg of benzethonium chloride, per vial.

Formulation Example 7

As a pharmaceutical component, about 50 mg (powder weight) of a lyophilized product of hPTH (1-84) preparation as acetic acid content being 2.5%, which was obtained in Example 5(2), was weighted out, and an injection solvent (Japanese Pharmacopoeia) was added thereto to obtain a hPTH (1-84) aqueous solution of 2 mg/mL as determined by reverse phase HPLC (25 mL).

On the other hand, WFI (Japanese Pharmacopoeia) was added to 2 g of purified sucrose (Japanese Pharmacopoeia) to obtain 100 mL of a purified sucrose aqueous solution. 20 mL of the hPTH (1-84) aqueous solution (2 mg/mL) and 20 mL of the prepared purified sucrose aqueous solution (2 w/v %) were mixed. The resulting solution was charged into each of 35 vials by lmL per vial and was freeze-dried in a freeze-drier, Model FZ-6 (Labconco Corporation), to obtain a stable pharmaceutical composition containing 1 mg of hPTH (1-84) and 10 mg of purified sucrose, per vial.

Formulation Example 8

An attached solvent, used for the pharmaceutical composition obtained in the aforementioned formulation examples 1 through 7 in a dissolved-upon-use type preparation, was prepared as follows.

0.35 g of benzalkonium chloride (Japanese Pharmacopoeia) and 21.0 g of citric acid (Japanese Pharmacopoeia) were weighed out and dissolved in 350 mL of purified water. 3 mL of the solution, thus obtained, was dispensed into each of polypropylene bottles to prepare an attached solvent.

Formulation Example 9

An attached solvent, used for the pharmaceutical composition obtained in the aforementioned formulation examples 1 through 7 in a dissolved-upon-use type preparation, was prepared as follows.

0.70 g of benzethonium chloride (Japanese Pharmacopoeia) and 14.0 g of citric acid (Japanese Pharmacopoeia) were weighed out and dissolved in 3500 mL of purified water. 3 mL of the solution thus obtained was dispensed into each of polypropylene bottles to prepare an attached solvent.

Formulation Example 10

An attached solvent, used for the pharmaceutical composition obtained in the aforementioned formulation examples 1 through 7 in a dissolved-upon-use type preparation, was prepared as follows.

0.35 g of benzethonium chloride (Japanese Pharmacopoeia) and 21.0 g of adipic acid (Japanese Pharmacopoeia) were weighed out and dissolved in 3500 mL of purified water. 3 mL of the solution thus obtained was dispensed into polypropylene bottles to prepare an attached solvent.

Formulation Example 11

An attached solvent, used for the pharmaceutical composition obtained in the aforementioned formulation examples 1 through 7 in a dissolved-upon-use type preparation, was prepared as follows.

0.70 g of cetylpyridium chloride (Japanese Pharmacopoeia) and 14.0 g of adipic acid (Japanese Pharmacopoeia) were weighed out and dissolved in 3500 mL of purified water. 3 mL of the solution thus obtained was dispensed into polypropylene bottles to prepare an attached solvent.

Formulation Example 12

As a pharmaceutical component, an amount of preparation corresponding to 900 mg as hPTH (1-34) obtained as acidic content being 2.5% in Example 4(1) (six vials) was dissolved in 18 mL of an WFI (Japanese Pharmacopoeia) (50 mg/mL). On the other hand, 12 g of citric acid (Japanese Pharmacopoeia) was dissolved in an injection solvent (Japanese Pharmacopoeia) to obtain 1000 mL of a solution (1.2 w/v % citric acid aqueous solution). Using the resulting solutions, liquid medicaments were obtained as follows.

1. Preparation of pH3, hPTH (1-34) 5 mg/mL, 0.6 w/v % Citric Acid Solution 6 mL of the 1.2 w/v % citric acid aqueous solution and 1.2 mL of the 50 mg/mL hPTH (1-34) aqueous solution were mixed and a pH of the resulting solution was adjusted to 3 by adding 95 μL of iN NaOH. Then, WFI was added to the solution to make a solution volume 12 mL. The solution, thus obtained, was filtered through a 0.22 μm filter to obtain the title pharmaceutical composition.

2. Preparation of pH3.5, hPTH (1-34) 5 mg/mL, 0.6 w/v % Citric Acid Solution 6 mL of the 1.2 w/v % citric acid aqueous solution and 1.2 mL of the 50 mg/mL hPTH (1-34) aqueous solution were mixed and a pH of the solution was adjusted to 3.5 by adding 210 μL of iN NaOH. Then, an WFI was added to the solution to make a solution volume 12 mL. The solution, thus obtained, was filtered through a 0.22 μm filter to obtain the title pharmaceutical composition.

3. Preparation of pH4, hPTH (1-34) 5 mg/mL, 0.6 w/v % Citric Acid Solution

6mL of the 1.2 w/v % citric acid aqueous solution and 1.2 mL of the 50 mg/mL hPTH (1-34) aqueous solution were mixed and a pH of the solution was adjusted to 4.0 by adding 350 μL of 1N NaOH. Then, WFI was added to the solution to make a solution volume 12 mL. The solution, thus obtained, was filtered through a 0.22 μm filter to obtain the title pharmaceutical composition.

4. Preparation of pH4.5, hPTH (1-34) lmg/mL, 0.4 w/v % Citric Acid Solution 4 mL of the 1.2 w/v % citric acid aqueous solution, 0.24 mL of the 50 mg/mL hPTH (1-34) aqueous solution, and about 5 mL of purified water were mixed and a pH of the solution was adjusted to 4.5 by adding 335 μL of 1N NaOH. Then, WFI was added to the solution to make a solution volume 12 mL. The solution, thus obtained, was filtered through a 0.22 μm filter to obtain the title pharmaceutical composition.

INDUSTRIAL APPLICABILITY

According to this invention, it is provided a pharmaceutical component which, being reduced of its content of acetic acid, is highly stable and will ensure an excellent use feeling when incorporated into a pharmaceutical component for usage.

The pharmaceutical component of this invention can tolerate the addition of appropriate amounts of various functional components, as well as a carrier or excipient which is usually used during pharmaceutical preparation, may be incorporated into pharmaceutical compositions of widely varied dosage forms, or may be shaped into widely varied dosage forms itself.

According to this invention, a pharmaceutical composition for intranasal administration is provided which is usable over a long period.

The invention claimed is:

1. A pharmaceutical component comprising a human parathyroid hormone peptide or its derivative, and acetic acid contained in an amount less than its chemical equivalent amount with respect to the human parathyroid hormone peptide or to its derivative, as calculated from the number of excess basic amino acid residues in the molecule of the human parathyroid hormone peptide or its derivative.

2. A pharmaceutical component as described in claim 1 comprising a salt of the human parathyroid hormone peptide or of its derivative with acetic acid wherein acetic acid is contained in an amount less than its chemical equivalent amount with respect to the human parathyroid hormone peptide or to its derivative.

3. A pharmaceutical component as described in claim 1, wherein the human parathyroid hormone peptide or its derivative is a peptide comprising the amino acid sequence of SEQ ID NO: 1.

4. A pharmaceutical component as described in claim 3, wherein the pharmaceutical component comprises 3 weight % or less acetic acid with respect to the weight of the peptide.

5. A pharmaceutical component as described in claim 1, wherein the pharmaceutical component is a lyophilized composition.

6. A pharmaceutical component as described in claim 1, wherein the pharmaceutical component is for intranasal administration.

7. A prior-to-use dissolvable pharmaceutical product comprising a lyophilized portion and a dissolving solution portion attached thereto wherein the pharmaceutical component as described in claim 1 is contained in the lyophilized portion.

8. A pharmaceutical component as described in claim 1, wherein the human parathyroid hormone peptide or its derivative is a peptide comprising the amino acid sequence of SEQ ID NO: 2.

9. A pharmaceutical component as described in claim 8, wherein the pharmaceutical component comprises 4 weight % or less acetic acid with respect to the weight of the peptide.

10. A pharmaceutical component as described in claim 8, wherein the pharmaceutical component comprises 6 weight % or less acetic acid with respect to the weight of the peptide.

11. A pharmaceutical composition for intranasal administration comprising a human parathyroid hormone peptide or its derivative and acetic acid contained in an amount less than its chemical equivalent amount with respect to the human parathyroid hormone peptide or to its derivative, as calculated from the number of excess basic amino acid residues in the molecule of the human parathyroid hormone peptide or its derivative.

12. A pharmaceutical component comprising a human parathyroid hormone peptide, and acetic acid contained in an amount less than its chemical equivalent amount with respect to the human parathyroid hormone peptide or to its derivative, as calculated from the number of excess basic amino acid residues in the molecule of the human parathyroid hormone peptide;

wherein the human parathyroid hormone peptide is selected from the group consisting of SEQ ID NO: 1 and SEQ ID NO: 2.

* * * * *

SEQUENCE LISTING

```
<160> NUMBER OF SEQ ID NOS: 2

<210> SEQ ID NO 1
<211> LENGTH: 84
<212> TYPE: PRT
<213> ORGANISM: Homosapiens
<220> FEATURE:
<223> OTHER INFORMATION: Amino acid sequence of human parathyroid
      hormone (hPTH(1-84))

<400> SEQUENCE: 1

Ser Val Ser Glu Ile Gln Leu Met His Asn Leu Gly Lys His Leu Asn
  1               5                  10                  15

Ser Met Glu Arg Val Glu Trp Leu Arg Lys Lys Leu Gln Asp Val His
                 20                  25                  30

Asn Phe Val Ala Leu Gly Ala Pro Leu Ala Pro Arg Asp Ala Gly Ser
             35                  40                  45

Gln Arg Pro Arg Lys Lys Glu Asp Asn Val Leu Val Glu Ser His Glu
         50                  55                  60

Lys Ser Leu Gly Glu Ala Asp Lys Ala Asp Val Asn Val Leu Thr Lys
 65                  70                  75                  80

Ala Lys Ser Gln

<210> SEQ ID NO 2
<211> LENGTH: 34
<212> TYPE: PRT
<213> ORGANISM: Homosapiens
<220> FEATURE:
<223> OTHER INFORMATION: Amino acid sequence of C-terminal truncated
      human parathyroid hormone (hPTH(1-34))

<400> SEQUENCE: 2

Ser Val Ser Glu Ile Gln Leu Met His Asn Leu Gly Lys His Leu Asn
  1               5                  10                  15
```

```
-continued

Ser Met Glu Arg Val Glu Trp Leu Arg Lys Lys Leu Gln Asp Val His
            20              25                  30
Asn Phe
```